United States Patent [19]

Young et al.

[11] Patent Number: 4,851,409
[45] Date of Patent: Jul. 25, 1989

[54] 2-SUBSTITUTED QUINOLINE DIOIC ACIDS AND PHARMACEUTICAL COMPOSITIONS

[75] Inventors: Robert N. Young, Senneville; Robert Zamboni, Longueuil; Serge Leger, Dollard des Ormeaux, all of Canada

[73] Assignee: Merck Frosst Canada Inc., Kirkland, Canada

[21] Appl. No.: 11,181

[22] Filed: Feb. 5, 1987

Related U.S. Application Data

[63] Continuation-in-part of Ser. No. 829,679, Feb. 14, 1986, abandoned.

[51] Int. Cl.$^4$ .................. A61K 31/47; A61K 31/535; C07D 215/14; C07D 413/12
[52] U.S. Cl. ...................... 514/228.2; 514/235.2; 514/252; 514/253; 514/311; 514/312; 514/313; 514/314; 424/45; 544/58.4; 544/80; 544/121; 544/128; 544/357; 544/363; 546/152; 546/153; 546/160; 546/162; 546/168; 546/170; 546/171; 546/172; 546/173; 546/174; 546/175; 546/176; 546/177; 546/178; 546/179; 546/156
[58] Field of Search ............... 544/58.4, 80, 121, 128, 544/357, 363; 546/152, 153, 156, 160, 162, 168, 170, 171, 172, 173, 174, 175, 176, 177, 178, 179; 514/228.2, 235.2, 252, 253, 311, 312, 313, 314; 424/45

[56] References Cited

U.S. PATENT DOCUMENTS

| | | | |
|---|---|---|---|
| 4,598,150 | 7/1986 | Fujisaki et al. | 546/152 |
| 4,661,499 | 4/1987 | Young et al. | 546/152 |

Primary Examiner—Robert W. Ramsuer
Attorney, Agent, or Firm—Gabriel Lopez; Hesna J. Pfeiffer

[57] ABSTRACT

Compounds having the formula:

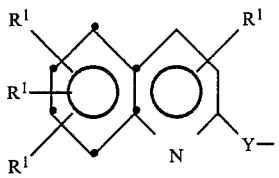

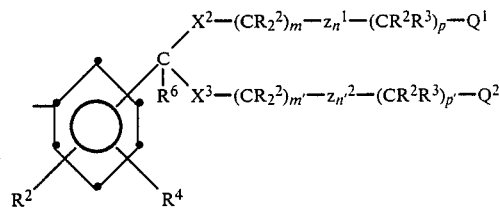

are antagonists of leukotrienes and inhibitors of their biosynthesis. These compounds are useful as anti-asthmatic, anti-allergic, anti-inflammatory, and cytoprotective agents.

9 Claims, No Drawings

2-SUBSTITUTED QUINOLINE DIOIC ACIDS AND PHARMACEUTICAL COMPOSITIONS

CROSS-REFERENCE

This is a CIP of U.S. Ser. No. 829,679, filed Feb. 14, 1986, pending.

The process of Method E is described and claimed in U.S. Ser. No. 011,166, filed on Feb. 5, 1987, entitled "Synthesis of Chiral Thioacetals and Thioethers", attorney docket no. 17529.

BACKGROUND OF THE INVENTION

This invention is directed to compounds which act as antagonists of the leukotrienes and inhibitors of their biosynthesis.

The leukotrienes and their biological activities, especially their roles in various disease states and conditions have been described. For example, see EP No. 140,684 (May 8, 1985), which is incorporated herein by reference.

Several classes of compounds exhibit ability to antagonize the action of leukotrienes in mammals, especially humans. See for example: United Kingdom Patent Specification Nos. 2,058,785 and 2,094,301; and European Patent Application Nos. 56,172, 61,800 and 68,739.

EP 110,405 (June 13, 1984) describes anti-inflammatory and antiallergic substituted benzenes which are disclosed to be leukotriene inhibitors, i.e., inhibitors of the 5-lipoxygenase pathway.

SUMMARY OF THE INVENTION

The present invention relates to compounds having activity as leukotriene and SRS-A antagonists or inhibitors, to methods for their preparation, to intermediates useful in their preparation and to methods and pharmaceutical formulations for using these compounds in mammals (especially humans).

Because of their activity as leukotriene antagonists or inhibitors, the compounds of the present invention are useful as anti-asthmatic, anti-allergic, and anti-inflammatory agents and are useful in treating allergic rhinitis and chronic bronchitis and for amelioration of skin diseases like psoriasis and atopic eczema. These compounds are also useful to antagonize or inhibit the pathologic actions of leukotrienes on the cardiovascular and vascular systems for example, actions such as result in angina. The compounds of the present invention are useful in the treatment of inflammatory and allergic diseases of the eye, including allergic conjunctivitis. The compounds are also useful as cytoprotective agents.

Thus, the compounds of the present invention may also be used to treat or prevent mammalian (especially, human) disease states such as erosive gastritis; erosive esophagitis; inflammatory bowel disease; ethanol-induced hemorrhagic erosions; hepatic ischemic; noxious agent induced damage or necrosis of hepatic, pancreatic, renal, or myocardial tissue; liver parenchymal damage caused by hepatoxic agents such as CCl$_4$ and D-galactosamine; ischemic renal failure; disease-induced hepatic damage; bile salt induced pancreatic or gastric damage; trauma- or stress-induced cell damage; and glycerol-induced renal failure.

DETAILED DESCRIPTION

The compounds of this invention are best realized by Formula I:

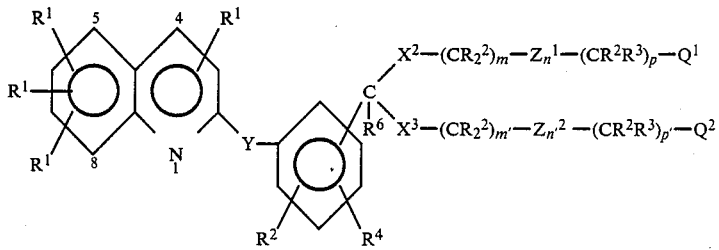

wherein:

R$^1$ is H, halogen, C$_1$–C$_8$ alkyl, C$_2$–C$_8$ alkenyl, C$_2$–C$_8$ alkynyl, —CF$_3$, —OR$^2$, SR$^2$, —S(O)R$^2$, —S(O)$_2$R$^2$, —NR$^2$R$^2$, —CHO, —COOR$^2$, —(C=O)R$^2$, —C(OH)R$^2$R$^2$, —CN, —NO$_2$, substituted or unsubstituted phenyl, substituted or unsubstituted benzyl, or substituted or unsubstituted phenethyl;

R$^2$ is H, C$_1$–C$_8$ alkyl, C$_2$–C$_8$ alkenyl, C$_2$–C$_8$ alkynyl, —CF$_3$, substituted or unsubstituted phenyl, substituted or unsubstituted benzyl, or substituted or unsubstituted phenethyl;

R$^3$ is H, halogen, —NO$_2$, —CN, —OR$^2$, —SR$^2$, NR$^2$R$^2$, or C$_1$–C$_8$ alkyl;

CR$^2$R$^3$ may be the radical of a naturally occurring amino acid;

R$^4$ is H, halogen, —NO$_2$, —CN, —OR$^2$, —SR$^2$, NR$^2$R$^2$, C$_1$–C$_8$ alkyl, or —(C=O)R$^2$;

R$^5$ is

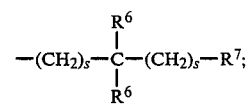

R$^6$ is H or C$_1$–C$_4$ alkyl;

R$^7$ is (A) a monocyclic or bicyclic heterocyclic radical containing from 3 to 12 nuclear carbon atoms and 1 or 2 nuclear heteroatoms selected from N, S or O and with each ring in the heterocyclic radical being formed of 5 or 6 atoms, or (B) the radical W-R$^8$;

R$^8$ contains up to 21 carbon atoms and is (1) a hydrocarbon radical or (2) an acyl radical of an organic acyclic or monocyclic carboxylic acid containing not more than 1 heteroatom in the ring;

R$^9$ is —OR$^{10}$, —SR$^{10}$, or NR$^{10}$R$^{10}$;

R$^{10}$ is H, C$_1$–C$_6$ alkyl, —(C=O)R$^{11}$, unsubstituted phenyl, unsubstituted benzyl, or two R$^{10}$ groups joined to the same N may form a ring of 5 or 6 members containing up to two heteratoms chosen from O, S or N;

R$^{11}$ is H, C$_1$–C$_8$ alkyl, C$_2$–C$_8$ alkenyl, C$_2$–C$_8$ alkynyl, —CF$_3$, or unsubstituted phenyl, benzyl, or phenethyl;

R$^{12}$ is R$^2$ or halogen;

m and m' are independently 0–8;

n and n' are independently 0 or 1;
p and p' are independently 0-8;
m+n+p is 1-10;
m'+n'+p' is 1-10;
s is 0-3;
$Q^1$ and $Q^2$ are independently —$COOR^2$, tetrazole, —$COOR^5$, —$CONHS(O)_2R^{11}$, —CN, —$CONR^{10}R^{10}$, —CHO, —$CH_2OH$, —$COCH_2OH$, —$NHS(O)_2R^{11}$; or if $Q^1$ or $Q^2$ is COOH and $R^3$ is —OH, —SH, or —$NHR^2$ then $Q^1$ or $Q^2$ and $R^3$ and the carbons through which they are attached may form a heterocyclic ring with loss of water;
W is O, S, or NH;
$X^1$ is O, S, —S(O)—, —$S(O)_2$—, —$NR^2$, or —$CR^2R^2$—;
$X^2$ and $X^3$ are independently O, S, S(O), or $S(O)_2$;
Y is —$CR^2=CR^2$—, —C≡C—, —$CR^2R^2$—$X^1$—, —$X^1$—$CR^2R^2$—, —$CR^2R^2$—$X^1$—$CR^2R^2$—,

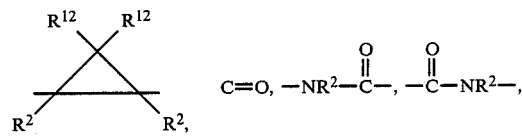

O, S, or —$NR^2$;
$Z^1$ and $Z^2$ are independently —$CONR^2$—; and the pharmaceutically acceptable salts thereof.

Alkyl, alkenyl, and alkynyl are intended to include linear, branched, and cyclic structures.

Alkyl groups include methyl, ethyl, propyl, isopropyl, butyl sec- and tert-butyl, pentyl, hexyl, heptyl, cyclopropyl, cyclobutyl, cyclopentyl, cyclohexyl, cycloheptyl, norbornyl and the like.

Alkenyl groups include vinyl, allyl, isopropenyl, pentenyl, hexenyl, heptenyl, cyclopropenyl, cyclobutenyl, cyclopentenyl, cyclohexenyl, cycloheptenyl, 1-propenyl, 2-butenyl, 2-methyl-2-butenyl, norbornenyl, and the like.

Substituted phenyl, benzyl, and phenethyl include 1 or 2 substituents on the benzene ring selected from $C_1$-$C_6$ alkyl, $R^9$, $NO_2$, $SCF_3$, halogen, —$COR^6$, —$COR^9$, CN, and $CF_3$.

Halogen includes F, Cl, Br and I.

The prodrug esters of Q (i.e., when Q=—$COOR^5$) are intended to include the esters such as are described by Saari et al., J. Med Chem., 21, No. 8, 746-753 (1978).

When Q and $R^3$ and the carbons through which they are attached form a ring, the rings thus formed include lactones, lactams, and thiolactones.

It is intended that the definitions of any substituent (e.g., $R^1$, $R^2$, m, Q, X, etc.) in a particular molecule be independent of its definitions elsewhere in the molecule. Thus, —$NR^2R^2$ represents —NHH, —$NHCH_3$, —$NHC_6H_5$, etc.

The heterocycles formed when two $R^{10}$ groups join through N include pyrrolidine, piperidine, morpholine, thiamorpholine, piperazine, and n-methylpiperazine.

The naturally occurring amino acids, the radicals of which may be $CR^2R^3$, include alanine, asparagine, aspartic acid, arginine, cysteine, glutamic acid, glutamine, glycine, histidine, isoleucine, leucine, lysine, methionine, phenylalanine, proline, serine, threonine, tryptophan, tyrosine and valine.

Examples of Z—$CR^2R^3$—Q containing a naturally occurring amino acid radical include:

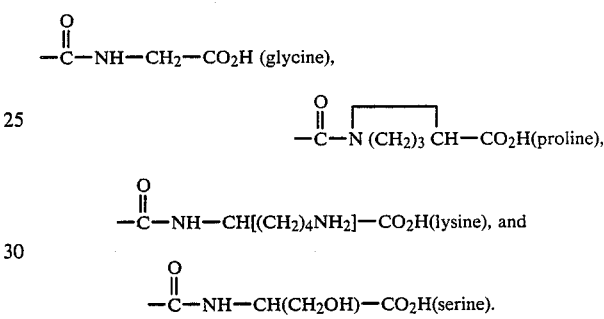

Some of the compounds described herein contain one or more centers of asymmetry and may thus give rise to diastereoisomers and optical isomers. The present invention is meant to comprehend such possible diastereoisomers as well as their racemic and resolved, optically active forms.

Some of the compounds described herein contain olefinic double bonds, and unless specified otherwise, are meant to include both E and Z geometric isomers.

Preferred compounds of Formula I are best represented by Formula Ia:

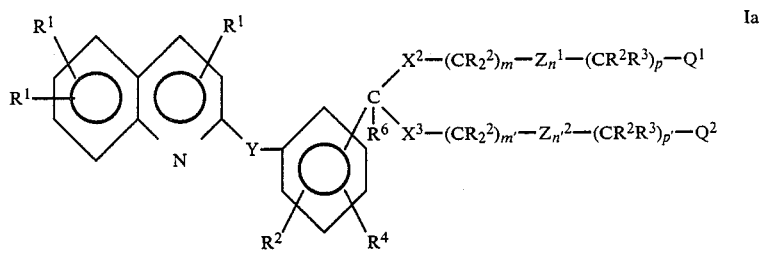

wherein:
Y is —$CR^2=CR^2$—, —C≡C—, $CR_2{}^2O$, or —$CR_2{}^2S$—; the other substituents are as defined for Formula I; and the pharmaceutically acceptable salts thereof.

More-preferred compounds of Formula I are best represented by Formula Ib:

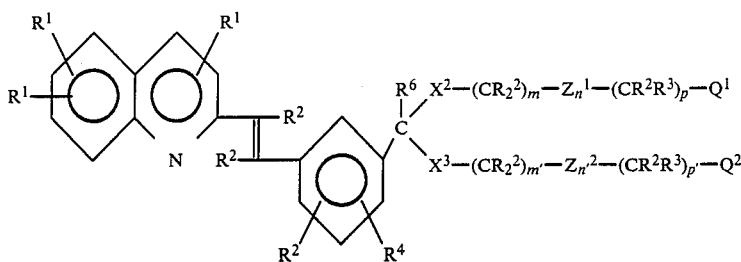

Ib wherein: $R^1$ is H, halogen, $C_1$-$C_3$ alkyl, —$CF_3$, or $SCF_3$;

$R^2$ is H, $C_1$-$C_3$ alkyl, $C_2$-$C_3$ alkenyl, or —$CF_3$;

$X^2$ and $X^3$ are independently O or S; the other substituents are as defined for Formula I; and the pharmaceutically acceptable salts thereof.

Other more-preferred compounds of Formula I are best represented by Formula Ic:

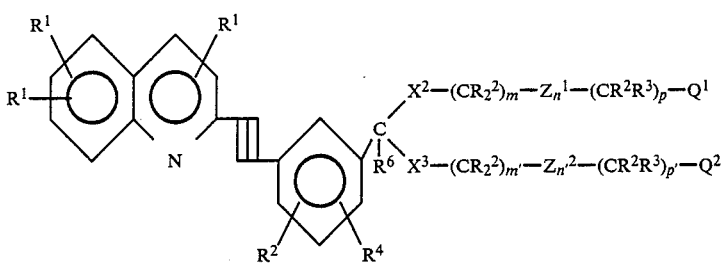

Ic wherein:

$R^1$ is H, halogen, $C_1$-$C_3$ alkyl, —$CF_3$, or $SCF_3$;

$R^2$ is H, $C_1$-$C_3$ alkyl, $C_2$-$C_3$ alkenyl, or —$CF_3$;

$X^2$ and $X^3$ are independently O or S; the other substituents are as defined for Formula I; and the pharmaceutically acceptable salts thereof.

Other more-preferred compounds within the scope of this invention are best represented by Formula Id:

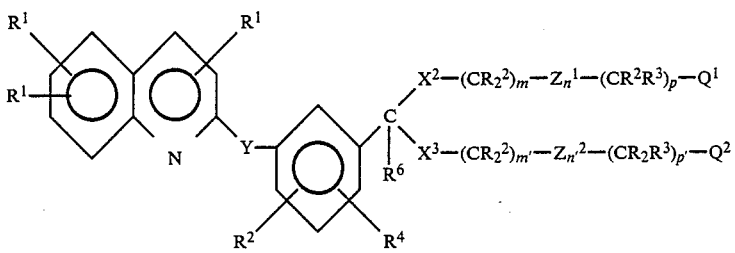

Id wherein:

$R^1$ is H, halogen, $C_1$-$C_3$ alkyl, $CF_3$ or $SCF_3$;

$R^2$ is H, $C_1$-$C_3$alkyl, $C_2$-$C_3$alkenyl, or $CF_3$;

$X^2$ and $X^3$ are independently O or S;

Y is —$CR_2^2O$— or —$CR_2^2S$—; the other substituents are as defined for Formula I; and the pharmaceutically acceptable salts thereof.

A preferred embodiment of compounds of formulae Ib, Ic, or Id is that wherein $Q^1$ or $Q^2$ is $COOR^2$, tetrazole, $COOR^5$, $CONR^{10}R^{10}$ or $COCH_2OH$, with the remaining substituent being defined as for Ib, Ic or Id, respectively.

The compounds of Formula I are active as antagonists of SRS-A and especially of leukotriene $D_4$. These compounds also have modest inhibitory activity on leukotriene biosynthesis but are primarily of therapeutic interest as antagonists. The activity of the compounds of Formula I can be detected and evaluated by methods known in the art. See for example, Kadin, U.S. Pat. No. 4,296,129.

The ability of the compounds of Formula I to antagonize the effects of the leukotrienes and to inhibit the leukotrienes makes them useful for inhibiting the symptoms induced by the leukotrienes in a human subject.

The compounds are valuable therefore in the prevention and treatment of such disease states in which the leukotrienes are the causative factor, e.g. skin disorders, allergic rhinitis, and obstructive airway diseases. The compounds are particularly valuable in the prevention and treatment of allergic bronchial asthma. They are also effective in the treatment of inflammatory diseases of the eye. It will be understood that in this paragraph and in the discussion of methods of treatment which follows, references to the compounds of Formula I are meant to include the pharmaceutically acceptable salts and lactone, lactam or thiolactone forms.

The cytoprotective activity of a compound may be observed in both animals and man by noting the increased resistance of the gastrointestinal mucosa to the noxious effects of strong irritants, for example, the ulcerogenic effects of aspirin or indomethacin. In addition to lessening the effect of non-steroidal anti-inflammatory drugs on the gastrointestinal tract, animal studies show that cytoprotective compounds will prevent gastric lesions induced by oral administration of strong acids, strong bases, ethanol, hypertonic saline solutions and the like.

Two assays can be used to measure cytoprotective ability. These assays are; (A) an ethanol-induced lesion assay and (B) an indomethacin-induced ulcer assay and are described in EP 140,684.

The magnitude of a prophylactic or therapeutic dose of a compound of Formula I will, of course, vary with the nature of the severity of the condition to be treated and with the particular compound of Formula I and its route of administration. It will also vary according to the age, weight and response of the individual patient. In general, the daily dose range for anti-asthmatic, anti-allergic or anti-inflammatory use and generally, uses other than cytoprotection, lie within the range of from about 0.001 mg to about 100 mg per kg body weight of a mammal, preferably 0.01 mg to about 10 mg per kg, and most preferably 0.1 to 1 mg per kg, in single or divided doses. On the other hand, it may be necessary to use dosages outside these limits in some cases.

The exact amount of a compound of the Formula I to be used as a cytoprotective agent will depend on, inter alia, whether it is being administered to heal damaged cells or to avoid future damage, on the nature of the damaged cells (e.g., gastrointestinal ulcerations vs. nephrotic necrosis), and on the nature of the causative agent. An example of the use of a compound of the Formula I in avoiding future damage would be co-administration of a compound of the Formula I with a non-steroidal anti-inflammatory drug that might otherwise cause such damage (for example, indomethacin). For such use, the compound of Formula I is administered from 30 minutes prior up to 30 minutes after administration of the NSAID. Preferably it is administered prior to or simultaneously with the NSAID, (for example, in a combination dosage form).

The effective daily dosage level for compounds of Formula I inducing cytoprotection in mammals, especially humans, will generally range from about 0.1 mg/kg to about 100 mg/kg, preferably from about 1 mg/kg to about 100 mg/kg. The dosage may be administered in single or divided individual doses.

Any suitable route of administration may be employed for providing a mammal, especially a human with an effective dosage of a leukotriene antagonist. For example, oral, rectal, topical, parenteral, ocular, nasal, buccal, and the like may be employed. Dosage forms include tablets, troches, dispersions, suspensions, solutions, capsules, creams, ointments, aerosols, and the like.

The pharmaceutical compositions of the present invention comprise a compound of Formula I as an active ingredient or a pharmaceutically acceptable salt thereof, and may also contain a pharmaceutically acceptable carrier and optionally other therapeutic ingredients. The term "pharmaceutically acceptable salts" refers to salts prepared from pharmaceutically acceptable non-toxic bases or acids including inorganic bases or acids and organic bases or acids.

Salts derived from inorganic bases include sodium, potassium, lithium, ammonium, calcium, magnesium, ferrous, zinc, copper, manganous, aluminum, ferric, manganic salts and the like. Particularly preferred are the ammonium, potassium, sodium, calcium and magnesium salts. Salts derived from pharmaceutically acceptable organic non-toxic bases include salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-dimethylaminoethanol, 2-diethylaminoethanol, tromethamine, lysine, arginine, histidine, caffeine, procaine, hydrabamine, choline, betaine, ethylenediamine, glycosamine, methylglucamine, theobromine, purines, piperazine, piperidine, N-ethylpiperidine, polyamine resins and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric acid, p-toluenesulfonic and the like. Particularly preferred are hydrobromic, hydrochloric, phosphoric and sulfuric acids.

The compositions include compositions suitable for oral, rectal, topical, parenteral (including subcutaneous, intramuscular, and intravenous), ocular (ophthalmic), pulmonary (nasal or buccal inhalation), or nasal administration, although the most suitable route in any given case will depend on the nature and severity of the conditions being treated and on the nature of the active ingredient. They may be conveniently presented in unit dosage form and prepared by any of the methods well-known in the art of pharmacy.

For use where a composition for intravenous administration is employed, a suitable dosage range for anti-asthmatic, anti-inflammatory or anti-allergic use is from about 0.001 mg to about 10 mg (preferably from about 0.01 mg to about 1 mg) of a compound of Formula I per kg of body weight per day and for cytoprotective use from about 0.1 mg to about 100 mg (preferably from about 1 mg to about 100 mg and more preferably from about 1 mg to about 10 mg) of a compound of Formula I per kg of body weight per day.

In the case where an oral composition is employed, a suitable dosage range for anti-asthmatic, anti-inflammatory or anti-allergic use is, e.g. from about 0.01 mg to about 100 mg of a compound of Formula I per kg of body weight per day, preferably from about 0.1 mg to about 10 mg per kg and for cyto-protective use from about 0.1 mg to about 100 mg (preferably from about 1 mg to about 100 mg and more preferably from about 10 mg to about 100 mg) of a compound of Formula I per kg of body weight per day.

For administration by inhalation, the compounds of the present invention are conveniently delivered in the form of an aerosol spray presentation from pressurized packs or a nebuliser, or as a powder which may be formulated as a cartridge from which the powder composition may be inhaled with the aid of a suitable device. The preferred delivery system for inhalation is a metered dose inhalation (MDI) aerosol, which may be formulated as a suspension or solution in fluorocarbon propellants.

Suitable topical formulations of Compound I include transdermal devices, aerosols, creams, ointments, lotions, dusting powders, and the like.

For the treatment of diseases of the eye, ophthalmic preparations for ocular administration comprising 0.001–1% by weight solutions or suspensions of the compounds of Formula I in an acceptable ophthalmic formulation may be used.

In practical use, the compounds of Formula I can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, capsules and tablets, with the solid oral preparations being preferred over the liquid preparations. Because of their ease of administration, tablets and capsules represent the most advantageous oral dosage unit form, in which case solid pharmaceutical carriers are obviously employed. If desired, tablets may be coated by standard aqueous or nonaqueous techniques.

In addition to the common dosage forms set out above, the compounds of Formula I may also be administered by controlled release means and/or delivery devices such as those described in U.S. Pat. Nos. 3,845,770; 3,916,899; 3,536,809; 3,598,123; 3,630,200 and 4,008,719, the disclosures of which are hereby incorporated herein by reference.

Pharmaceutical compositions of the present invention suitable for oral administration may be presented as discrete units such as capsules, cachets or tablets each containing a predetermined amount of the active ingredient, as a powder or granules or as a solution or a suspension in an aqueous liquid, a non-aqueous liquid, an oil-in-water emulsion or a water-in-oil liquid emulsion. Such compositions may be prepared by any of the methods of pharmacy but all methods include the step of bringing into association the active ingredient with the carrier which constitutes one or more necessary ingredients. In general, the compositions are prepared by uniformly and intimately admixing the active ingredient with liquid carriers or finely divided solid carriers or both, and then, if necessary, shaping the product into the desired presentation. For example, a tablet may be prepared by compression or molding, optionally with one or more accessory ingredients. Compressed tablets may be prepared by compressing in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Desirably, each tablet contains from about 2.5 mg to about 500 mg of the active ingredient and each cachet or capsule contains from about 2.5 to about 500 mg of the active ingredient.

The following are examples of representative pharmaceutical dosage forms for the compounds of Formula I:

| Injectable Suspension (I.M.) | mg/ml |
|---|---|
| Compound of Formula I | 10 |
| Methylcellulose | 5.0 |
| Tween 80 | 0.5 |
| Benzyl alcohol | 9.0 |
| Benzalkonium chloride | 1.0 |
| Water for injection to a total volume of 1 ml | |

| Tablet | mg/tablet |
|---|---|
| Compound of Formula I | 25 |
| Microcrystalline Cellulose | 415 |
| Providone | 14.0 |
| Pregelatinized Starch | 43.5 |
| Magnesium Stearate | 2.5 |
| | 500 |

| Capsule | mg/capsule |
|---|---|
| Compound of Formula I | 25 |
| Lactose Powder | 573.5 |
| Magnesium Stearate | 1.5 |
| | 600 |

In addition to the compounds of Formula I, the pharmaceutical compositions of the present invention can also contain other active ingredients, such as cyclooxygenase inhibitors, non-steroidal anti-inflammatory drugs (NSAIDs), peripheral analgesic agents such as zomepirac, diflunisal and the like. The weight ratio of the compound of the Formula I to the second active ingredient may be varied and will depend upon the effective dose of each ingredient. Generally, an effective dose of each will be used. Thus, for example, when a compound of the Formula I is combined with an NSAID the weight ratio of the compound of the Formula I to the NSAID will generally range from about 1000:1 to about 1:1000. Combinations of a compound of the Formula I and other active ingredients will generally also be within the aforementioned range, but in each case, an effective dose of each active ingredient should be used.

NSAIDS can be characterized into five groups:
(1) the propionic acid derivatives;
(2) the acetic acid derivatives;
(3) the fenamic acid derivatives;
(4) the biphenylcarboxylic acid derivatives; and
(5) the oxicams or a pharmaceutically acceptable salt thereof. NSAIDs which are within the scope of this invention are those disclosed in EP No. 140,684.

Pharmaceutical compositions comprising the Formula I compounds may also contain inhibitors of the biosynthesis of the leukotrienes such as are disclosed in EP No. 138,481 (Apr. 24, 1985), EP No. 115,394 (Aug. 8, 1984), EP No. 136,893 (Apr. 10, 1985), and EP No. 140,709 (May 5, 1985), which are hereby incorporated herein by reference.

The compounds of the Formula I may also be used in combination with leukotriene antagonists such as those disclosed in EP No. 106,565 (Apr. 25, 1984) and EP No. 104,885 (Apr. 4, 1984) which are hereby incorporated herein by reference and others known in the art such as those disclosed in European patent application Nos. 56,172 (July 21, 1982) and 61,800 (Oct. 6, 1982); and in U.K. Patent Specification No. 2,058,785, which are hereby incorporated herein by reference.

Pharmaceutical compositions comprising the Formula I compounds may also contain as the second active ingredient prostaglandin antagonists such as those disclosed in European patent applications 11,067 (May 28, 1980), 166,591 (Jan. 2, 1986) or thromboxane antagonists such as those disclosed in U.S. Pat. No. 4,237,160. They may also contain histidine decarboxylase inhibitors such as α-fluoromethyl-histidine, described in U.S. Pat. No. 4,325,961. The compounds of the Formula I may also be advantageously combined with an $H_1$ or $H_2$-receptor antagonist, such as for instance benadryl, dramamine, histadyl, phenergan, terfenadine, acetamazole, cimetidine, ranitidine, famotidine, aminothiadiazoles disclosed in EP No. 40,696 (Dec. 2, 1981) and like compounds, such as those disclosed in U.S. Pat. Nos. 4,283,408; 4,362,736; and 4,394,508. The pharmaceutical compositions may also contain a K+/H+ ATPase inhibitor such as omeprazole, disclosed in U.S. Pat. No. 4,255,431, and the like. Another useful pharmaceutical composition comprises the Formula I compounds in combination with serotonin antagonists such as methysergide, the serotonin antagonists disclosed in Nature, vol. 316, pages 126-131, 1985, and the like. Each of the references referred to in this paragraph is hereby incorporated herein by reference.

Compounds of the present invention can be prepared according to the following methods.

In these schemes, the 2-substituted quinoline radical

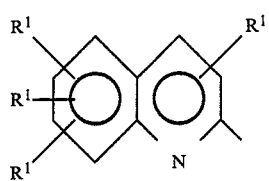

is represented by "2SQ—".

METHOD A

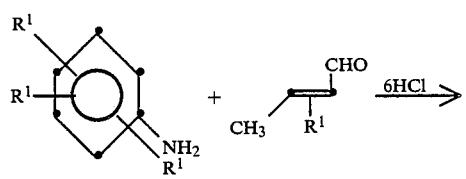

II

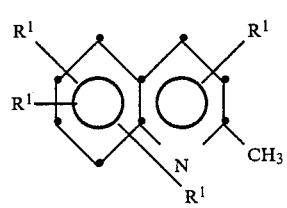

III

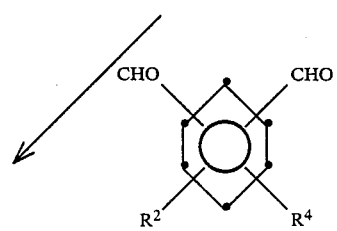

IV

-continued
METHOD A

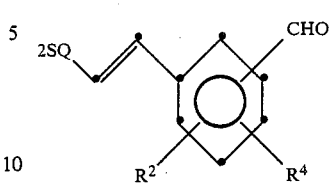

V $$HX^2-(CR_2^2)_m-Z_n^1-(CR^2R^3)_p-Q^1$$
$$HX^3-(CR_2^2)_{m'}-Z_{n'}^2-(CR^2R^3)_{p'}-Q^2$$
$$X^2, X^3 = O, S$$

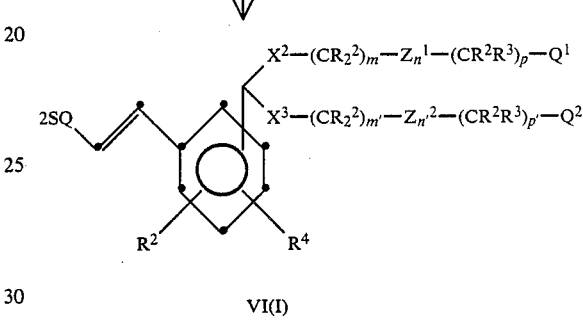

VI(I)

METHOD B $$HX^2-(CR_2^2)_m-Z_n^1-(CR^2R^3)_p-Q^1$$
IV $\xrightarrow{HX^3-(CR_2^2)_{m'}-Z_{n'}^2-(CR^2R^3)_{p'}-Q^2}{BF_3.OEt \text{ or } TMS-Cl}$

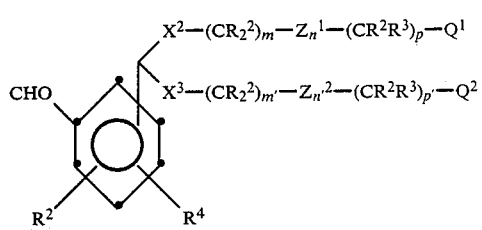

VII

2SQ—CH3
III

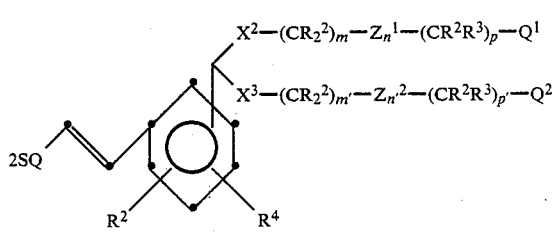

VI(I)

METHOD C

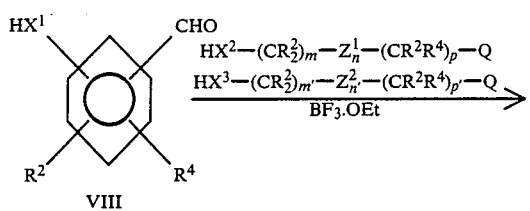

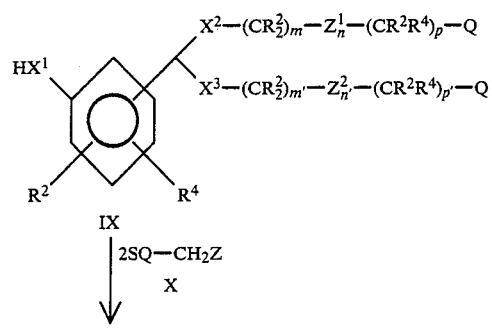

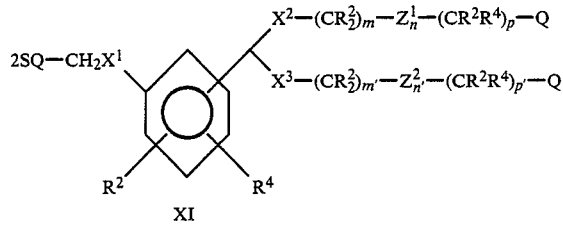

METHOD D

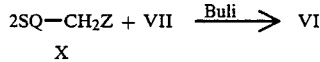

Z = halogen

Z = Ph₃P⁺

METHOD E

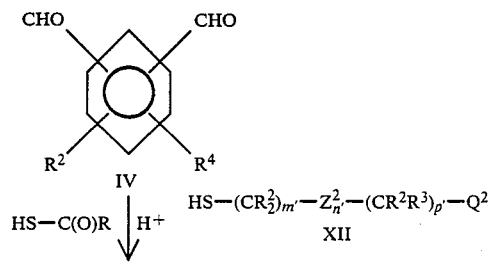

METHOD E -continued

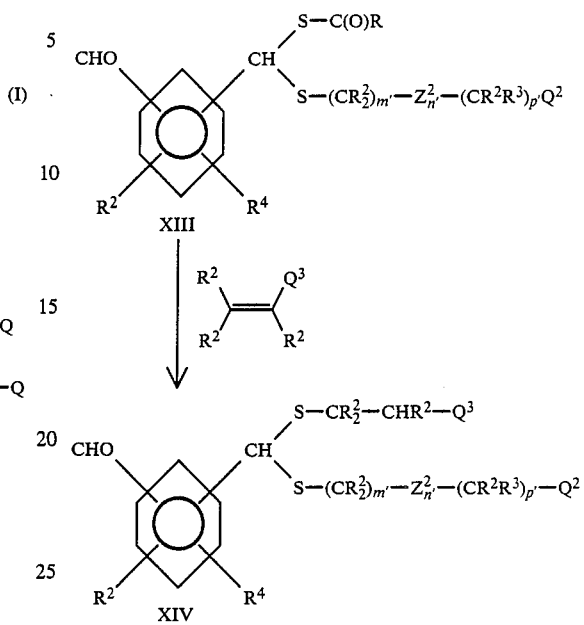

METHOD A:

Referring to Method A, an aniline derivative of Formula II is reacted by heating with a crotonaldehyde and a strong mineral acid such as aqueous hydrochloric acid to provide the substituted quinaldine derivative of structure III. When II is unsymmetrical two regioisomers of III may be obtained. The products are purified by precipitation of the zinc chloride adducts or by standard chromatographic techniques. Quinaldine III is reacted with isophthalaldehyde derivative IV by heating with a dehydrating agent, most preferably by heating with acetic anhydride, to provide the 2-styryl quinoline derivative of structure V. Reaction of the styrylaldehyde V with an alkanoic acid or tetrazole terminally substituted with a thiol or hydroxy group in an inert solvent such as benzene in the presence of a suitable catalyst such as BF₃.OEt affords the stryrylquinoline derivative VI, which is a representative of structure I.

METHOD B:

Alternatively an isophthalaldehyde derivative of structure IV is reacted with an alkanoic acid or tetrazole terminally substituted with a thiol or hydroxy group in an inert solvent such as benzene in the presence of a suitable catalyst such as BF₃.OEt or trimethyl silylchloride to afford the acetal derivative VII. Quinoline derivative III is condensed with aldehyde VII by heating with a dehydrating agent, preferably acetic anhydride, to provide the 2-styrylquinoline ketal of structure VI, which is a representative of structure I.

METHOD C:

Aldehyde VIII is reacted with an alkanoic acid or tetrazole terminally substituted with a thiol or hydroxy group in an inert solvent such as benzene in the presence of a suitable catalyst such as BF₃.OEt to afford the acetal derivative IX. The acetal derivative IX is then reacted with a quinaldine derivative of general structure X, in which Z is a leaving group such as Br or methanesulfonate, in the presence of a suitable base such as NaOH, NaH, K₂CO₃ in an inert solvent such as THF, dioxane, DMF, etc., with warming if necessary to provide adducts XI. The required quinaldine X is prepared by standard methods from quinaldine derivatives of formula III.

METHOD D:

An alternative preparation of compound VI is to convert a quinaldine derivative X (Z=halogen) to X (Z=Ph3P+) to form a Wittig reagent, which may be reacted with a base such as butyl lithium and the aldehyde VII to produce VI.

METHOD E:

An alternate preparation of compounds of type XIV, a subtype of VII, is as follows. A dialdehyde of structure IV is reacted with one equivalent of the appropriate thiol XII and one equivalent of thiol acid, RC(O)SH, in a solvent such as benzene with an acid such as p-toluenesulfonic acid to give the compound of general structure XIII which is purified by chromatography. The purified XIII is reacted in methanol or ethanol preferably at low temperature but also up to room temperature with a base such as NaOMe (or NaOH or Na2CO3) followed by a Michael aceptor olefin to give asymmetric thioacetal XIV.

In Method E, $Q^3$ is —COOR$^2$, —COOR$^5$, —CN, —CONR$^{10}$R$^{10}$ or CHO and R is $C_1$-$C_{12}$ alkyl, phenyl or substituted phenyl, or is the radical from an optically active carboxylic acid such as α-methoxy phenylacetic acid, abietic acid, camphoric acid, cis-2-benzamidocyclohexane carboxylic acid, diacetyl tartaric anhydride, α-methoxy-α-trifluoromethylphenylacetic acid, menthyloxyacetic acid, 2-methylbutyric acid, 2-phenylbutyric acid, 2-phenylpropionic acid or pyrogutamic acid.

In cases where VI or XI contains an ester group, they may be hydrolyzed in a mixture of a polar solvent such as THF and a strong base such as aqueous sodium hydroxide to provide the respective salts, acidification of which provides the corresponding acids. These salts and acids are also representatives of structure I.

The invention is further defined by reference to the following examples, which are intended to be illustrative and not limiting.

All temperatures are in degrees Celsius.

In Table 1 are shown some representative Formula I compounds.

TABLE 1

Compounds of Formula I

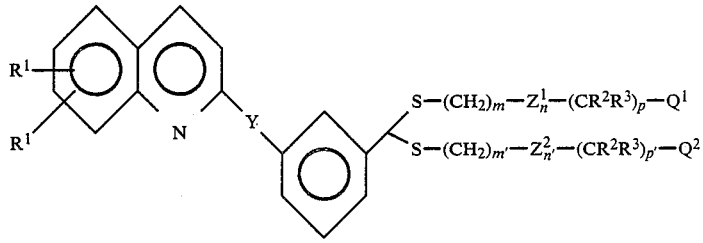

Ie

| Example | R$^1$,R$^1$ | m,m' | Y | $Z_n^1$—(CR$^2$R$^3$)$_p$—Q$^1$ | $Z_{n'}^2$—(CR$^2$R$^3$)$_{p'}$—Q$^2$ |
|---|---|---|---|---|---|
| 1 | H,7-Cl | 2,2 | —CH=CH— | —COOH | —COOH |
| 2 | H,7-Br | 2,2 | —CH=CH— | —COONa | —COONa |
| 3 | H,7-Cl | 2,2 | —CH$_2$O— | —COOH | —COOH |
| 4 | H,7-Cl | 2,2 | —CH=CH— | —COC(CH$_3$)$_2$ | —COONa |
| 5 | H,7-Cl | 2,2 | —CH=CH— | tetrazole-H | tetrazole-H |
| 5(1) | H,7-Cl | 2,2 | —CH=CH— | —CN | —CN |
| 6 | H,7-Cl | 2,2 | —CH=CH— | —CONH$_2$ | —COOH |
| 7 | H,7-Cl | 2,2 | —CH=CH— | CONHCH$_2$CO$_2$H | —COOH |
| 8 | H,7-Cl | 2,2 | —CH=CH— | —CONHCH$_3$ | —COOH |
| 9 | H,7-Cl | 2,2 | —CH=CH— | —CON(C$_2$H$_5$)$_2$ | —COOH |
| 10 | H,7-Cl | 2,2 | —CH$_2$O— | —CON(CH$_3$)$_2$ | —COOH |
| 11 | H,7-Cl | 2,2 | —CH=CH— | —CON(morpholino) | —COOH |
| 12 | H,7-Cl | 1,1 | —CH=CH— | —COOH | —COOH |
| 13 | H,7-Cl | 1,1 | —CH=CH— | —CON(CH$_3$)$_2$ | —COOH |
| 14 | H,H | 2,2 | —CH=CH— | —COOH | —COOH |
| 15 | 6-Cl,7-Cl | 2,2 | —CH=CH— | —COOH | —COOH |
| 16 | H,7-Cl | 2,2 | —CH$_2$O— | —COOH | —CONH—t-Bu |
| 17 | H,7-Cl | 2,2 | —CH$_2$O— | —CONH$_2$ | —COOH |
| 18 | H,7-Cl | 2,2 | —CH$_2$O— | —CONHMe | —COOH |
| 19 | H,7-Cl | 2,2 | —CH$_2$CH$_2$CH$_2$— | —COONa | —COONa |
| 20 | H,7-Cl | 2,2 | —CH$_2$S— | —COOH | —CON(CH$_3$)$_2$ |
| 21 | H,7-Cl | 2,2 | —CH$_2$S— | —COOH | —CONH$_2$ |

TABLE 1-continued
Compounds of Formula I

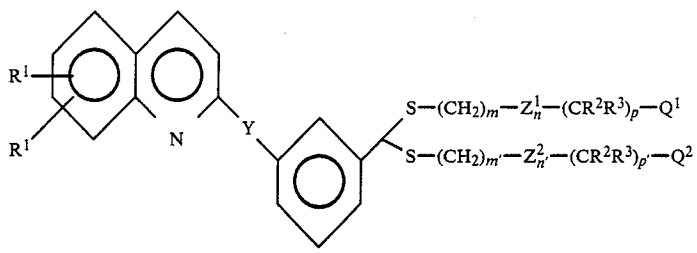

Ie

| Example | R¹,R¹ | m,m' | Y | $Z_n^1$—$(CR^2R^3)_p$—$Q^1$ | $Z_{n'}^2$—$(CR^2R^3)_{p'}$—$Q^2$ |
|---|---|---|---|---|---|
| 22 | H,7-Cl | 2,2 | —CH₂O— | (tetrazole-O-linked, H) | —CONH—t-Bu |
| 22(1) | H,7-Cl | 2,2 | —CH₂O— | —CN | —COOH |
| 22(2) | H,7-Cl | 2,2 | —CH₂O— | —CN | —CONH—t-Bu |
| 23 | H,7-Cl | 2,2 | —CH₂O— | —CONH₂ | —CONH₂ |
| 24 | H,7-Cl | 2,2 | —CH—CH₂—CH— | —COOH | —COOH |
| 25 | H,7-Cl | 2,2 | —CH₂CH₂— | —COOH | —COOH |
| 26 | H,7-Cl | 2,2 | —CH₂CH₂— | —CON(CH₃)₂ | —COOH |
| 27 | H,7-Cl | 2,2 | —CH=CH— | —COOH | —CON(CH₃)₂ (+)-isomer |
| 28 | H,7-Cl | 2,2 | —CH=CH— | —COOH | —CON(CH₃)₂ (+)-isomer |
| 29 | H,7-Cl | 0,0 | —CH=CH— | —CH(CH₃)CH₂COOH | —CH(CH₃)—CH₂COOH |
| 30 | H,7-Cl | 0,0 | —CH₂O— | —C(CH₃)₂CH₂COOH | —C(CH₃)₂CH₂COOH |
| 31 | H,7-CF₃ | 2,2 | —CH=CH— | —COOH | —CON(CH₃)₂ |
| 32 | H,6-SO₂Me | 2,2 | —CH₂O— | —COOH | —CONH—t-Bu |
| 33 | H,7-F | 2,2 | —CH₂S— | —COOH | —COOH |
| 34 | H,6-CN | 2,2 | —CH=CH— | —CONH₂ | —CONH₂ |
| 35 | H,7-Cl | 2,2 | —CH=CH— | —COOH | —CONHS(O₂)Me |
| 36 | 6-F,7-F | 2,2 | —CH₂O— | —CH₂OH | —COOH |
| 37 | H,7-SCF₃ | 2,2 | —CH=CH— | —CH₂OH | —COOH |
| 38 | H,7-S(O)₂CF₃ | 2,2 | —CH₂S— | —CHO | —COOH |
| 39 | H,7-Cl | 1,1 | —CH₂O— | —COOH | —COOH |
| 40 | H,7-Cl | 1,1 | —CH₂O— | —COONa | —CON(CH₃)₂ |
| 41 | H,7-Cl | 1,1 | —CH₂O— | —COOH | —CONH₂ |
| 42 | H,7-F | 2,2 | —CH₂O— | —COOH | —COOH |
| 43 | H,7-F | 2,2 | —CH₂O— | —COOH | —CON(CH₃)₂ |
| 44 | H,7-CF₃ | 2,2 | —CH₂O— | —COOH | —COOH |
| 45 | H,7-CF₃ | 2,2 | —CH₂O— | —COOH | —CON(CH₃)₂ |
| 46 | H,7-CH₃ | 2,2 | —CH=CH— | —COOH | —CON(CH₃)₂ |

EXAMPLE 1

5-(3-(2-(7-CHLOROQUINOLIN-2-YL)ETHENYL)-PHENYL)-4,6-DITHIANONANEDIOIC ACID

Step 1

Preparation of dimethyl 5-(3-formylphenyl)-4,6-dithianonanedioate

To a solution of isophthalaldehyde (5.4 g) in CHCl₃ (50 ml) and methyl 3-mercaptopropanoate (9.2 ml) was added dropwise trimethylsilylchloride (6.5 ml). The reaction mixture was stirred 1 hour at room temperature, quenched with aqueous NH₄OAc (25%), and extracted with ethylacetate. Flash chromatography of the residue using 1:1 ethylacetate hexane afforded the title compound.

p.m.r. (CD₃COCD₃) δ: 2.6–3.0 (m, 8H); 3.60 (s, 6H); 5.5 (s, 1H); 7.6 (t, 1H); 7.8–8.0 (m, 2H); 8.05 (m, 1H); 10.05 p.p.m. (s, 1H).

Step 2

Preparation of dimethyl 5-(3-(2-(7-chloroquinolin-2-yl)ethenyl)phenyl)-4,6-dithianonanedioate A solution of aldehyde (Step 1) (5.2 g) and 7-chloroquinaldine were heated in 45 ml acetic anhydride for 48 hours. The reaction mixture was evaporated. Flash chromatography of the residue using 5% ethylacetate in hexane afforded the title compound.

p.m.r. (CD₃COCD₃) δ: 2.6–3.0 (m, 8H); 3.65 (s, 6H); 5.32 (s, 1H); 7.4–7.6 (m, 4H); 7.65 (m, 1H); 7.85–8.05 (m, 5H); 8.35 p.p.m. (d, 1H).

Step 3

To a solution of dimethyl ester (Step 2) (1.7 g) in 1,2-dimethoxyethane (60 ml) was added lithium hydroxide (10 ml of 2N). The reaction mixture was stirred overnight at room temperature. H₂O (100 ml) was added and the 1,2-dimethoxyethane was removed under vacuo. The solution was extracted with ethylacetate (300 ml). The aqueous phase was acidified to pH 3, extracted with ethylacetate (200 ml), dried and evaporated. Flash chromatography of the residue using 5%

EtOH in CH₂Cl₂ with 1% of acetic acid afforded the title compound.

p.m.r. (CD₃COCD₃+3 drops CD₃SOCD₃) δ: 2.6–3.0 (m, 8H); 5.35 (s, 1H); 7.4–7.55 (m, 4H), 7.6–7.7 (m, 1H); 7.8–8.05 (m, 5H) and 8.35 p.p.m. (d, 1H).

EXAMPLE 2

DISODIUM 5-(3-(2-(7-BROMOQUINOLIN-2-YL)ETHENYL)-PHENYL)-4,6-DITHIANONANEDIOIC ACID

Step 1

Preparation of dimethyl-5-(3-(2-(7-bromoquinolin-2-yl)ethenyl)-phenyl)-4,6-dithianonanedioic acid Using the procedure of Example 1 (Step 2), but substituting 7-bromoquinaldine for 7-chloroquinaldine was obtained the title compound.

p.m.r. (CD₃COCD₃) δ: 2.6–3.0 (m, 8H); 3.65(s, 6H); 5.35 (s, 1H); 7.4–7.55 (m, 3H); 7.6–7.7 (m, 2H); 7.8–7.95 (m, 4H); 8.2 (d, 1H); 8.3 p.p.m. (d, 1H).

Step 2

To a solution of dimethyl ester (Step 1) (1 g) in THF (10 ml) and EtOH (10 ml) at room temperature was added 3 ml of 2N NaOH. The reaction mixture was stirred 2 days at room temperature. The solution was evaporated. Purification of the residue by reverse phase HPLC (Waters C₁₈ μ-bondapak column) using H₂O/MeOH (35:65) buffered at pH 5.5 afforded the title compound contaminated with salts. The residue was dissolved in aqueous NaOH and applied on an XAD-8 column. The column was first eluted with H₂O. Elution with ethanol afforded the title compound.

p.m.r. (CD₃SOCD₃) δ: 2.3–2.9 (m, 8H); 5.30 (s, 1H); 7.3–7.5 (m, 2H); 7.6–8.0 (m, 7H); 8.15 (d, 1H); 8.35 p.p.m. (d, 1H).

EXAMPLE 3

5-(3-((7-CHLOROQUINOLIN-2-YL-METHYL)OXY)PHENYL)-4,6-DITHIANONANEDIOIC ACID

Step 1

Preparation of dimethyl 5-(3-hydroxyphenyl)-4,6-dithianonanedioate

To a solution of 3-hydroxybenzaldehyde (3.6 g) and methyl 3-mercaptopropanoate (8.0 ml) in benzene (100 ml) was added boron trifluoride etherate (1.0 ml). The reaction mixture was stirred overnight at room temperature, quenched with aqueous NH₄OAc, extracted with ether, dried and evaporated. Flash chromatography of the residue using 40% ethyl acetate in hexane afforded the title compound.

p.m.r. (CDCl₃) δ: 2.5–3.0 (m, 8H); 3.7 (s, 6H); 4.8 (s, 1H); 6.3 (bs, 1H); 6.8–7.2 p.p.m. (m, 4H).

Step 2

Preparation of 2-bromomethyl-7-chloroquinoline

A stirred suspension of N-bromosuccinimide (9.0 g), 7-chloroquinaldine (9.0 g), dibenzoylperoxide (0.5 g) in CCl₄ (200 ml) at 90° was illuminated with a 225 W sunlamp for 6 hours. The suspension was cooled and passed through a plug of silica gel. The plug of silica gel was washed with 30% ether in hexane and the filtrate was evaporated. Flash chromatography of the residue using 30% ether in hexane afforded the title compound.

p.m.r. (CDCl₃) δ: 4.3 (s, 2H); 7.0–8.0 p.p.m. (m, 5H).

Step 3

Preparation of dimethyl 5-(3-((7-chloroquinolin-2-yl-methyl)oxy)phenyl)-4,6-dithianonanediote A mixture of 2-bromomethyl-7-chloroquinoline (2.5 g) (Step 2), phenol (Step 1) (3.4 g) and K₂CO₃ (3 g) was heated at reflux for 4 hours in methyl ethyl ketone (100 ml). The reaction mixture was cooled and ether (100 ml) was added. The suspension was filtered and evaporated. Flash chromatography of the residue using 30% ethyl acetate in hexane afforded the title compound.

p.m.r. (CD₃COCD₃) δ: 2.6–3.0 (m, 8H); 3.60 (s, 6H); 5.2 (s, 1H); 5.35 (s, 2H); 7.0 (m, 1H); 7.1 (1H; 7.2–7.3 (m, 2H); 7.5–7.6 (1H); 7.7–7.75 (d, 1H); 8.0 (d, 1H); 8.05 (d, 1H); 8.4 p.p.m. (d, 1H).

Step 4

Using the procedure of Example 1 (Step 3) but substituting the compound of Example 3 (Step 3) for the diester of Example 1 (Step 2) there was obtained the title compound.

p.m.r. (CD₃COCD₃) δ: 2.5–2.9 (m, 8H); 5.25 (s, 1H); 5.4 (s, 2H); 7.0 (m, 1H); 7.1 (d, 1H); 7.2–7.35 (m, 2H); 7.6 (s, 1H); 7.75 (s, 1H); 8.0 (d, 1H); 8.05 (d, 1H); 8.45 p.p.m. (d, 1H).

EXAMPLE 4

5-(3-(2-(7-CHLOROQUINOLIN-2-YL)ETHENYL)-PHENYL)-8-DIMETHYLCARBAMYL-4,6-DITHIAOCTANOIC ACID SODIUM SALT

Step 1

Preparation of 2-bromomethyl-7-chloroquinoline

A solution of 7-chloroquinaldine (177 g, 1 mole) N-bromosuccinimide (178 g, 1 mole), benzoylperoxide (1 g) in 2 L CCl₄ were heated at reflux for 2 days under a sun lamp. The reaction mixture was cooled, and passed through a plug of SiO₂ (approx. 1 Kg) using toluene as eluent. Chromatography on 2×1 kg SiO₂ columns using toluene as eluent afforded 110–120 g of the title compound, m.p. 112°(d).

p.m.r. (CDCl₃) δ: 8.3 (d, 1H), 8.1–7.9 (m, 2H), 7.4–7.7 (m, 2H); 4.7 p.p.m. (s, 2H).

Step 2

Preparation of (7-chloroquinolin-2-yl)-methyltriphenylphosphonium bromide

To a suspension of 2-bromomethyl-7-chloroquinoline (120 g, 0.5 mol) in 800 mL CH₃CN at 60° was added triphenylphosphine (183 g). The reaction mixture was heated overnight at 60°, cooled and 400 mL ether was added. The solid was filtered and dried to yield 170 g phosphonium salt.

p.m.r. (CDCl₃) δ: 7.3–8.2 (m, 20H); 6.0 p.p.m. (d, 2H).

Step 3

Preparation of dimethyl 5-(3-formylphenyl)-4,6-dithianonanedioate

To a solution of isophthalaldehyde (40 g, 0.3 mol.) in chloroform (400 mL) and methyl 3-mercaptopropanoate (68 mL, 0.6 mol.) was added dropwise trimethylsilyl chloride (48 mL, 0.38 mol.) over 30 min. The reaction mixture was stirred at R.T. for 2 hours. The reaction was quenched with 25% aq. NH₄OAc, extracted with ethyl acetate dried and evaporated. Flash chromatography of the residue afforded 50 g of the title compound.
p.m.r. (CD$_3$COCD$_3$) δ: 10.05 (s, 1H), 8.05 (m, 1H), 7.85 (t, 2H), 7.6 (t, 1H), 5.4 (s, 1H), 3.6 (s, 6H), 2.6–3.0 p.p.m. (m, 8H).

Step 4

Preparation of dimethyl 5-(3-(2-(7-chloroquinolin-2-yl)ethenyl)phenyl)-4,6-dithianonanedioate To a suspension of 190 g phosphonium salt from Step 2 (0.36 mol.) in THF (2 L) at −78° was added 1.6 M BuLi (220 mL) dropwise over 1.5 hrs. The resulting brown suspension was stirred 30 min at −78°. To the suspension was added the aldehyde (Step 3) (117 g, 0.32 mol.) in THF (400 mL) dropwise over 1.5 hrs. The reaction mixture was allowed to warm to room temperature and quenched with pH 7 buffer (approx. 2 L). Ethyl acetate (1 L) was added. The organic phase was seperated, dried and evaporated. Flash chromatography of the residue using 30% ethyl acetate hexane; followed by crystallization with 3:1 hexane/ether afforded 135 g of the title compound as a white solid.
m.p. 53°, p.m.r. (CD$_3$COCD$_3$) δ: 8.3 (d, 1H), 8.2 (d, 1H), 7.8–7.95 (m, 4H), 7.6–7.7 (m, 2H), 7.4–7.6 (m, 3H), 5.4 (s, 1H), 3.65 (s, 6H), 2.6–3.0 p.p.m. (m, 8H).

Step 5

Preparation of methyl 5-(3-(2-(7-chloroquinolin-2-yl)ethenyl)phenyl)-8-dimethylcarbamyl-4,6-dithiaoctanoate A solution of the aluminum reagent was prepared by adding dropwise 150 mL of 2 M trimethylaluminum in hexane at −20° to a solution of 2 M dimethylamine in toluene (300 mL). The solution was allowed to warm to room temperature.

To the diester (step 4) (95 g) in CH$_2$Cl$_2$ (1 L) was added dropwise 150 mL of the aluminum reagent. The reaction was stirred 7–8 hrs at room temperature. The reaction was carefully quenched at 0° with 2N HCl (until the vigorous reaction subsided); then pH 7 buffer (25% NH$_4$OAc in H$_2$O) (1 L) and CH$_2$Cl$_2$ (1 L) were added. The organic phase was separated, dried and evaporated. Flash chromatography of the residue using first 50% ethyl acetate hexane followed by ethyl acetate afforded 38 g recovered di-ester and 38 g desired amide. The recovered di-ester was recycled through the sequence to give 18 g di-ester and 14 g desired amide. Total yield: 52 g of amide.
p.m.r. (CD$_3$COCD$_3$) δ: 8.3 (d, 1H), 7.8–8.0 (m, 5H), 7.6–7.7 (d, 1H), 7.4–7.65 (m, 4H), 5.45 (s, 1H), 3.6 (s, 6H), 2.95 (s, 3H), 2.85 (s, 3H), 2.6–3.0 p.p.m. (m, 8H).

Step 6:

Preparation of 5-(3-(2-(7-chloroquinolin-2-yl)ethenyl)phenyl)-8-dimethylcarbamyl-4,6-dithiaoctanoic acid To the amide (30 g) in 800 mL DME was added 1.5 eq 1N LiOH (75 mL). The reaction mixture was stirred one hour under N$_2$. The DME was evaporated. The residue was partitioned between H$_2$O (500 mL) and ethyl acetate (1 L). The aqueous phase was re-extracted with ethyl acetate (500 mL). The aqueous phase was acidified with AcOH and a little 2N HCl to pH 4 and extracted with ethyl acetate (2×600 mL). The organic phase was dried and evaporated. The residue was co-evaporated with toluene (300 mL) and triturated with cold ethyl acetate to give 18 g of the acid.
m.p. 153°–155°, p.m.r. (CD$_3$COCD$_3$+CD$_3$SOCD$_3$) δ: 8.4 (d, 1H), 7.8–8.05 (m, 5H), 7.7 (d, 1H), 7.4–7.6 (m, 4H), 5.35 (s, 1H), 2.95 (s, 3H), 2.85 (s, 3H), 2.5–2.95 p.p.m. (m, 8H).
Anal. calc'd. for C$_{26}$H$_{27}$ClN$_2$O$_3$S$_2$: C 60.63; H 5.28; N 5.44; S 12.45; Cl 6.88.
Found: C 60.43; H 5.23; N 5.63; S 12.56; Cl 6.62.

Step 7

To 32 g of acid (Step 6) in ethanol (500 mL) was added NaOH (31 mL of 2N). The reaction mixture was stirred at room temperature 1 hr and filtered. The filtrate was evaporated and co-evaporated 2× with ethanol and dried on a high vacuum pump. Crystallization from 4:1 THF/hexane afforded the title compound as a white solid.
p.m.r. (CD$_3$SOCD$_3$+CD$_3$COCD$_3$) δ: 8.35 (d, 1H), 8.0 (d, 1H), 7.95 (d, 1H), 7.90 (d, 1H), 7.85 (m, 2H), 7.3–7.7 (m, 5H), 5.28 (s, 1H), 2.9 (s, 3H), 2.8 (s, 3H), 2.55–2.8 (m, 6H), 2.2 p.p.m. (t, 2H).

EXAMPLE 5

5-(4-(3-(2-(7-CHLOROQUINOLIN-2-YL)ETHENYL)PHENYL)-7-(1H-TETRAZOL-5-YL)-3,5-DITHIAHEPTYL)-1H-TETRAZOLE

Step 1

Preparation of 5-(3-(2-(7-chloroquinolin-2-yl)ethenyl)phenyl)-4,6-dithianona-1,9-dinitrile To a solution of 5-(3-(2-(7-chloroquinolin-2-yl)ethenyl)phenyl)-4,6-dithianonadioic acid (Example 1) (500 mg) triethylamine in chloroform (11 mL) at −25° was slowly added a solution of ethyl chloroformate (0.7 mL) in chloroform (10 mL). The reaction was stirred at −25° for 20 min and then ammonia was bubbled into the reaction for 5 minutes, a white solid being formed. The reaction was stirred for 10 min at room temperature and THF (50 mL) was added. The reaction was filtered in celite and evaporated. To the solution of the residue in THF (20 mL) were added slowly pyridine (1.0 mL) followed by trifluoroacetic anhydride (1.0 mL). The reaction was stirred for 20 minutes. A 1 to 1 mixture of ethyl acetate and hexane was added to the reaction and it was filtered on a silica gel pad. The solvents were removed by evaporation and the resulting residue was purified by flash chromatography using 30% of ethyl acetate in hexane to afford the title compound as a white solid.
p.m.r. ((CD$_3$)$_2$CO) δ: 2.8 to 3.1 (m, 8H), 5.5 (s, 1H), 7.4–7.6 (m, 3H), 7.7 (d, 1H), 7.85–8.05 (m, 6H), 8.35 p.p.m. (d, 1H).

Step 2

To a solution of 5-(3-(2-(7-chloroquinolin-2-yl)ethenyl)phenyl)-4,6-dithianona-1,9-dinitrile from Step 1 (290 mg) in acetone (8 mL) was added tri-n-butyltinazide (630 mg). The solvent was removed from the reaction by evaporation and the resulting residue was stirred and heated at 120° for 1 hour. The reaction was diluted with ethanol (5 mL) and acetic acid (12 drops). The reaction was stirred 30 minutes at room temperature and ethyl acetate (20 mL), water (20 mL) and aqueous sodium hydroxide 2N (until pH 11) were added. The aqueous layer was separated and acidified with aqueous hydrochloric acid 2N until pH 3. The product was extracted from this aqueous layer using ethyl acetate. The organic layer was then dried over sodium sulfate and evaporated. The residue was purified by flash chromatography using 1% of acetic acid in a mixture of 30% ethanol in toluene to afford the title compound which was co-evaporated once with ethanol to give the title compound as a yellow solid.

p.m.r. ((CD$_3$)$_2$CO) 2.9 to 3.2 (m, 4H), 3.3 (t, 4H), 5.3 (s, 1H), 7.4–7.6 (m, 5H), 7.5 (d, 1H), 7.8–8.0 (m, 4H), 8.4 p.p.m. (d, 1H).

EXAMPLE 6

5-(3-(2-(7-CHLOROQUINOLIN-2-YL)ETHENYL)-PHENYL)-8-CARBAMYL-4,6-DITHIAOCTANOIC ACID

Using the procedure of Example 4 but substituting ammonia for dimethylamine in Step 5 there was obtained the title compound.

p.m.r. (CD$_3$COCD$_3$+CD$_3$SOCD$_3$) δ: 8.3 (d, 1H), 8.0 (d, 1H), 7.95 (d, 1H), 7.8–7.9 (m, 4H), 7.7 (m, 1H), 7.4–7.6 (m, 4H), 5.3 (s, 1H), 2.7–3.0 (m, 4H), 2.6 (m, 2H), 2.45 p.p.m. (m, 2H).

EXAMPLE 7

N-(8-CARBOXYL-5-(3-(2-(7-CHLOROQUINOLIN-2-2L)ETHENYL)PHENYL)-4,6-DITHIAOCTANOYL)LYCINE

Using the procedure of Example 16 but substituting methyl glycinate for t-butylamine in Step 3 is obtained the title compound as a methyl ester. The ester is hydrolyzed to the title compound.

EXAMPLE 8

5-(3-(2-(7-CHLOROQUINOLIN-2-YL)ETHENYL)-PHENYL)-4,6-DITHIA-8-METHYLCARBAMOYLOCTANOIC ACID

Using the procedure described in Example 4 but substituting methylamine for dimethylamine in Step 5 there was obtained the title compound.

p.m.r. (CD$_3$COCD$_3$) δ: 8.35 (d, 1H), 8.05 (d, 1H), 7.85–7.95 (m, 4H), 7.65 (dd, 1H), 7.4–7.6 (m, 4H), 7.1 (bs, 1H), 5.30 (s, 1H), 2.6–3.0 (m, 9H), 2.50 p.p.m. (t, 2H).

EXAMPLE 9

5-(3-(2-(7-CHLOROQUINOLINY-2-YL)ETHENYL)PHENYL)-8-DIETHYLCARBAMYL-4,6-DITHIAOCTANOIC ACID

Using the procedure described in Example 4 but substituting diethylamine for dimethylamine in Step 5 there was obtained the title compound.

p.m.r. (CD$_3$COCD$_3$) δ: 8.3 (d, 1H), 7.7–8.0 m, 5H), 7.3–7.6 (m, 5H), 5.2 (s, 1H), 3.1–3.3 (m, 4H), 2.4–2.7 (m, 6H), 2.0 (t, 3H), 1.9–2.1 p.p.m. (m, 6H).

EXAMPLE 10

5-(3-(7-CHLOROQUINOLIN-2-YLMETHOXY)-PHENYL)-8-DIMETHYLCARBAMYL-4,6-DITHIAOCTANOIC ACID

Using the procedure described in Example 4, Steps 5 and 6 but substituting the diester from Example 3, Step 3 for the diester from Example 4, Step 4 there was obtained the title compound.

p.m.r. (CD$_3$COCD$_3$) δ: 8.35 (d, 1H), 7.95 (dd, 1H), 7.9 (d, 1H), 7.5–7.65 (m, 2H), 7.2 (t, 1H), 7.05 (bs, 1H), 6.9 (m, 2H), 5.28 (s, 2H), 5.1 (s, 1H), 2.8 (s, 3H), 2.7 (s, 3H), 2.2–2.7 p.p.m. (m, 8H).

EXAMPLE 11

5-(3(2-(7-CHLOROQUINOLIN-2-YL)ETHENYL)-PHENYL-4,6-DITHIA-8-MORPHOLINOCARBAMYL-OCTANOIC ACID

Using the procedure of Example 4 but substituting morpholine for dimethyl amine in Step 5 there was obtained the title compound.

$^1$H NMR (250 MHz, CDCl$_3$) δ : 2.6 (2H, t, J=6 Hz), 2.7 (2H, t, J=6 Hz), 2.8–3.05 (4H, complex m), 3.38 (2H, t, J=4 Hz), 3.6 (6H, s(b)), 5.1 (1H, s), 7.15–7.80 (9H, complex m), 8.1 (2H, d, J=6 Hz), 8.7 (1H, s(b), exchangeable).

Anal. Calc'd. for C$_{28}$H$_{29}$ClN$_2$O$_4$S$_2$: C, 60.36; H, 5.25; N, 5.03; S, 11.51; Cl, 6.36.

Found: C, 60.40; H, 5.32; N, 4.86; S, 11.37; Cl, 6.66.

EXAMPLE 12

4-(3-(2-(7-CHLOROQUINOLIN-2-YL)ETHENYL)-PHENYL)-3,5-DITHIAHEPTACIOIC ACID

Using the procedure of Example 1 but substituting methyl 2-mercaptoacetate for methyl 3-mercaptopropanoate in Step 1 there was obtained the title compound.

p.m.r. (CD$_3$SOCD$_3$) δ: 3.3 (m, 4H), 5.25 (s, 1H), 7.25–7.95 (m, 10H), 8.30 p.p.m. (d, 1H).

EXAMPLE 13

4-(3-(2-(7-CHLOROQUINOLIN-2-YL)ETHENYL)-PHENYL)-6-DIMETHYLCARBAMYL-3,5-DITHIAHEXANOIC ACID

Using the procedure of Example 4 by substituting methyl 2-mercaptoacetate for methyl 3-mercaptopropanoate in Step 3 there was obtained the title compound.

$^1$H NMR (250 MHz, CDCl$_3$) δ: 2.9 (s, 3H), 3.0 (s, 3H), 3.3–3.5 (4 peaks, 2H), 3.65 (d, 2H), 5.5 (s, 1H), 7.2–7.65 (m, 7H), 7.7 (d, 1H, J=6 Hz), 7.8 (s, 1H), 8.05–8.10 (m, 2H), 8.8 (s, 1H, exchangeable).

Anal. Calc'd. for C$_{24}$H$_{23}$ClN$_2$O$_3$S$_2$: C, 59.18; H, 4.76; n, 5.75; S, 13.17; Cl, 7.28.

Found: C, 59.36; H, 4.96; N, 5.39; S, 12.98; Cl, 7.26.

EXAMPLE 14

5-(3-(2-(QUINOLIN-2-YL)ETHENYL)PHENYL)-4,6-DITHIANONANEDIOIC ACID

Using the procedure described in Example 1 but substituting quinaldine for 7-chloroquinaldine in Step 1 there was obtained the title compound.

p.m.r. (CD$_3$COCD$_3$) δ: 8.3 (d, 1H), 7.4–8.0 (m, 11H), 5.35 (s, 1H), 2.7–3.0 (m, 4H), 2.6 p.p.m. (m, 4H).

EXAMPLE 15

5-(3-(2-(6,7-DICHLOROQUINOLIN-2-YL)ETHENYL)PHENYL)-4,6-DITHIANONANEDIOIC ACID

Using the procedure described in Example 1 but substituting 6,7-dichloroquinaldine for 7-chloroquinaldine in Step 1 there was obtained the title compound.

p.m.r. (CD$_3$SOCD$_3$) δ: 8.3 (d, 1H), 8.15 (d, 2H), 7.8–8.0 (m, 3H), 7.65 (bd, 1H), 7.4–7.7 (m, 3H), 5.35 (s, 1H), 2.5–3.0 p.p.m. (m, 8H).

EXAMPLE 16

8-t-BUTYLCARBAMYL-5-(3-(7-CHLOROQUINOLIN-2-YLMETHOXY)PHENYL)-4,6-DITHIAOCTANOIC ACID

Step 1

Preparation of 3-(7-chloroquinolin-2-yl-methoxy)benzaldehyde

A mixture of the bromide (Example 4, Step 1) (109 g) and m-hydroxybenzaldehyde (45 g) and $K_2CO_3$ (96 g) in acetone 1.5 L were heated at 80° with stirring in an oil bath for 1.5 hours. The reaction mixture was cooled, $CH_2Cl_2$ (600 mL) was added, and the mixture was filtered and evaporated. Trituration of the residue with 7:1 ether/hexane afforded the title compound which was used as such for the next step.

p.m.r. ($CDCl_3$, 250 MHz) δ 9.55 (s, 1H), 8.2 (d, 1H), 8.10 (d, 1H), 7.75 (d, 1H), 7.65 (d, 1H). 7.4–7.6 (m, 4H), 7.28 (m, 1H), 5.4 p.p.m. (s, 2H),

Step 2

Preparation of 5-(3-(7-chloroquinolin-2-ylmethoxy)phenyl-4,6-dithianonanedioic acid A mixture of aldehyde (Step 1) (91 g, 0.3 mol.) in benzene (1.5 L), 3-mercaptopropanoic acid (100 mL) and toluene sulfonic acid (17 g) were refluxed with a Dean Stark trap for 4 hrs. The reaction mixture was cooled. The mixture was dissolved with 1N NaOH (1 L). The organic layer was separated and discarded. The aqueous layer was acidified to pH 6 with 2N HCl and extracted with ethyl acetate (2 × 1 L). The organic layer was dried and evaporated. Swishing the residue with ether (2 × 1 L) and filtration afforded the title di-acid (110 g). m.p. 142° p.m.r. ($CD_3COCD_3+CD_3SOCD_3$, 250 MHZ) δ: 8.45 (d, 1H), 8.0–8.1 (m, 2H), 7.75 (d, 1H), 7.63 (dd, 1H), 7.25–7.35 (m, 4H), 7.15 (d, 1H), 7.0 (dd, 1H), 5.4 (s, 2H), 5.25 (s, 1H), 2.6–2.9 (m, 4H), 2.55 p.p.m. (t, 4H).

Step 3

To a solution of di-acid (Step 2) (55 g, 0.114 mol.), triethylamine (35mL), in $CH_2Cl_2$ (2.8 l) and $CH_3CN$ (500 mL) at 0° was added 2-chloro-1-methylpyridinium iodide (32 g, 0.126 m). The suspension was stirred 1 hr at 0° to afford a yellow solution. To this solution was added t-butylamine (14 mL). The reaction was stirred at room temperature overnight. The mixture was then evaporated, and partitioned between ethyl acetate and $H_2O$. The aqueous phase was adjusted to pH 3–4 before extraction. The organic phase was dried and evaporated. Flash chromatography of the residue using 15% acetone and 0.2% AcOH in toluene afforded the title compound as an oil. Trituration with ethanol afforded the title compound as a white solid which was further purified by swishing in ether.

p.m.r. ($CD_3COCD_3$, 250 MHz) 8.25 (d, 1H), 7.95 (d, 1H), 7.8 (d, 1H), 7.65 (d, 1H), 7.55 (dd, 1H), 7.1–7.3 (m, 3H), 7.05 (s, 1H), 6.9 (m, 1H), 5.3 (s, 2H), 5.1 (s, 1H), 2.7–3.0 (m, 4H), 2.3–2.5 (m, 4H), 1.3 p.p.m. (s, 9H).

Anal. Calc'd. for $C_{27}H_{31}ClN_2O_4S_2$: C 59.27; H 5.71; N 5.12; S 11.72.

Found: C 58.71; H 5.97; N 5.12; S 11.78.

EXAMPLE 17

8-CARBAMYL-5-(3-(7-CHLOROQUINOLIN-2-YLMETHOXY)PHENYL)-4,6-DITHIAOCTANOIC ACID

The diacid (Example 3) (3.954 g, 8.04 mmoles) was dissolved in 250 mL $CH_2Cl_2:CH_3CN$ 4:1. Triethylamine (2.5 mL, 2.2 equiv.) was added followed, at 0° C., by 2-chloro-1-methylpyridinium iodide (2.257 g, 1.1 equiv.). After stirring 1 hour at 0° C., ammonia was added and the mixture stirred for another hour at 10° C. Water was then added and the aqueous layer acidified to pH 5. Extraction with $CH_2Cl_2$ (2×) and EtOAc (2×) and the flash chromatography of the residue on silica with acetone:$CH_2Cl_2$:AcOH 40:60:1 and 50:50:1 afforded the title compound.

$^1$H NMR ($CD_2Cl_2$:DMSO) δ: 2.23 (t, 2H), 2.32 (t, 2H), 2.44–2.68 (m, 4H), 4.90 (s, 1H), 5.20 (s, 2H), 6.33 (broad s, 1H), 6.77 (dd, 1H), 6.89 (d, 1H), 6.98–7.14 (m, 3H), 7.38 (dd, 1H), 7.53 (d, 1H), 7.74 (d, 1H), 7.88 (d, 1H), 8.15 (d, 1H) p.p.m.

EXAMPLE 18

5-(3-(7-CHLOROQUINOLIN-2-YLMETHOXY)-PHENYL)-4,6-DITHIA-8-METHYLCARBAMYLOCTANOIC ACID

Using the procedure described in Example 16 by replacing methylamine for t-butylamine in Step 3 there was obtained the title compound. p.m.r. ($CD_3COCD_3$) δ: 8.4 (d, 1H), 8.05 (d, 1H), 8.05 (d, 1H), 7.75 (d, 1H), 7.6 (dd, 1H), 7.4 (bs, 1H), 6.95–7.30 (4H), 5.2 (s, 1H), 5.4 (s, 1H), 2.6–2.9 (m, 7H), 2.6 (t, 2H), 2.4 p.p.m. (t, 2H).

EXAMPLE 19

5-(3-(3-(7-CHLOROQUINOLIN-2-YL)PROPYL)-PHENYL)-4,6-DITHIANONANEDIOIC ACID DISODIUM SALT

Step 1

Preparation of 3-ethenylbenzaldehyde

To a suspension of methyltriphenylphosphonium bromide (27.2 g) in THF (200 mL) at 0° was added dropwise n-butyllithium (47 mL of 1.6M in hexane). The reaction mixture was stirred 30 min at 0° and cooled to −10°. The reaction mixture at −10° was transferred dropwise through a canula to a solution of isophthaladehyde (10.0 g) in THF (300 mL) at −50°. The reaction was allowed to warm up to room temperature. After 3.5 hours at room temperature the reaction mixture was quenched with $NH_4OAc$ buffer (200 mL). The reaction mixture was extracted with ethyl acetate, dried over sodium sulfate and evaporated. Flash chromatography of the residue starting with 10% and finishing with 15% of diethyl ether in hexane afforded the title compound.

p.m.r. (($CD_3$)$_2CO$) δ: 5.37 (d, 1H), 5.96 (d, 1H), 6.87 (dd, 1H), 7.58 (t, 1H), 7.82 (m, 2H), 8.00 (t, 1H), 10.06 p.p.m. (s, 1H).

Step 2

Preparation of 2-(3-ethenylphenyl)-1,3-dioxolane

To a solution of 3-ethenylbenzaldehyde from Step 1 (3.77 g) and ethylene glycol (1.8 mL) in benzene (40 mL) was added p-toluenesulfonic acid monohydrate (100 mg). The reaction mixture was heated to reflux for 6 hours. The water produced by the reaction was collected in a Dean-Stark trap. The reaction was allowed to cool to room temperature. The reaction was diluted with NH₄OAc buffer and extracted with ethyl acetate. The organic layer was dried over sodium sulfate and evaporated. Flash chromatography of the residue using 15% diethyl ether in hexane afforded the title compound.

p.m.r. ((CD$_3$)$_2$CO) δ: 4.0 (m, 4H), 5.4 (d, 1H), 5.27 (s, 1H), 5.83 (d, 1H), 6.77 (dd, 1H), 7.35 (bs, 2H), 7.45 (bm, 1H), 7.54 p.p.m. (bs, 1H).

Step 3

Preparation of 2-(3-(2-hydroxethyl)phenyl)-1,3-dioxolane

To a solution of 2-(3-ethenylphenyl)-1,3-dioxolane from Step 2 (4.14 g) in THF (25 mL) was slowly added a solution of borane-tetrahydrofuran complex (8.3 mL of 0.98M solution in THF) at such a rate as to maintain the temperature of the reaction below 35°. A solution of aqueous sodium hydroxyde (2.5 mL of 3N) was carefully added followed by a solution of hydrogen peroxide (2.5 mL of 30% w/v in water). The reaction was stirred at room temperature for 30 min. A saturated aqueous solution of sodium chloride was added and the reaction was extracted with ethyl acetate. The organic layer was separated, dried over sodium sulfate and evaporated. Purification of the residue, by flash chromatography using 45% ethyl acetate in hexane afforded the title compound.

p.m.r. ((CD$_3$)$_2$CO) δ: 2.82 (t, 2H), 3.73 (m, 2H), 3.76 (t, 1H), 4.02 (m, 4H), 5.70 (s, 1H), 7.27 (m, 3H), 7.33 p.p.m. (bs, 1H).

Step 4

Preparation of 3-(1,3-dioxolane-2-yl)phenylacetaldehyde

To a solution of pyridine (7.5 mL) in dichloromethane (110 mL) at 10° was added chromium trioxide (4.85 g) and celite (16.0 g). After 15 minutes of stirring at 10°, a solution of the alcohol from Step 3 (1.11 g) in dichloromethane (11 mL) was added to the reaction. The resulting brown suspension was stirred for 20 min and sodium bisulfate (10 g) was added. After 30 min, diethyl ether (150 mL) was added and the reaction was vigorously stirred. The reaction was filtered on a pad of magnesium sulfate covered with silica gel. The solid removed by filtration was washed with diethyl ether (2×50 mL). Evaporation of the filtrate gave a colorless oil used as such in the next step.

Step 5

Preparation of 2-(3-(3-(7-chloroquinolin-2-yl)prop-2[E]-enyl)phenyl-1,3-dioxolane To a suspension of (7-chloroquinolin-2-yl)methyltriphenylphosphonium bromide (Example 4, Step 2) (2.70 g) in THF (30 mL) at −78° was added dropwise over 30 min a solution of butyl lithium (3.2 mL of 1.6M in hexane) to give a deep red-orange solution. A solution of the aldehyde from step 4 (0.85 g) in THF (10 mL) was added dropwise to the reaction at −78°. The reaction was stirred at −78° for 15 min and at room temperature for 45 min. The reaction was quenched with NH₄OAc buffer, extracted with ethyl acetate, dried over sodium sulfate and evaporated. The residue was purified by flash chromatography using 15% ethyl acetate in hexane to afford the title compound.

p.m.r. ((CD$_3$)$_2$CO) δ: 3.7 (dd, 2H), 4.0 (m, 4H), 5.7 (s, 1H), 6.8 (dt, 1H), 7.1 (dt, 1H), 7.3 (m, 3H), 7.4 (s, 1H), 7.5 (dd, 1H), 7.7 (d, 1H), 7.9 (m, 2H), 8.3 p.p.m. (d, 1H).

Step 6

Preparation of 2-(3-(3-(7-chloroquinolin-2-yl)propyl)phenyl)-1,3-dioxolane

To a solution of 2-(3-(3-(7-chloroquinolin-2-yl)prop-2[E]-enyl)phenyl)-1,3-dioxolane from Step 5 (168 mg) in a 1 to 1 mixture of ethyl acetate and hexane (12 mL) was added 5% rhodium-on-carbon (58 mg). The resulting black suspension was stirred under an atmosphere of hydrogen for 3.5 hours. The reaction was filtered on a pad of silica gel, washed with ethyl acetate (5 mL) and evaporated. The residue was purified by flash chromatography using 15% ethyl acetate in hexane to afford the title compound.

p.m.r. ((CD$_3$)$_2$CO) δ: 2.2 (m, 2H), 2.7 (t, 2H), 3.0 (t, 2H), 4.0 (m, 4H), 5.7 (s, 1H), 7.3 (m, 3H), 7.35 (s, 1H), 7.45 (d, 1H), 7.5 (dd, 1H), 7.9 (d, 1H), 7.95 (d, 1H), 8.25 p.p.m. (d, 1H).

Step 7

Preparation of 3-(3-(7-chloroquinolin-2-yl)propyl)benzaldehyde

To a solution of 2-(3-(3-(7-chloroquinolin-2-yl)propyl)phenyl)-1,3-dioxolane from Step 6 (189 mg) in THF (9.5 mL) was added a 1 to 1 mixture of acetic acid and water (6.5 mL). The reaction was heated at 63° for 2 hours. The reaction was diluted with ethyl acetate and the organic layer washed with saturated aqueous solution of sodium bicarbonate. The organic layer was dried over sodium sulfate and evaporated. The residue was co-evaporated once with toluene to afford the title compound.

p.m.r. ((CD$_3$)$_2$CO) δ: 2.2 (m, 2H), 2.8 (t, 2H), 3.0 (t, 2H), 7.5 (m, 3H), 7.6 (m, 1H), 7.7 (dd, 1H), 7.8 (m, 1H), 7.9 (d, 1H), 8.0 (d, 1H), 8.3 (d, 1H), 10.0 p.p.m. (s, 1H).

Step 8

To a solution of 3-(3-(7-chloroquinolin-2-yl)propyl)benzaldehyde from Step 7 (167 mg) in toluene (6 mL) was added 3-mercaptopropanoic acid (190 μL) and p-toluenesulfonic acid monohydrate (60 mg). The reaction was heated to reflux and the water produced by the reaction was removed with a Dean-Stark trap. The reaction was allowed to cool to room temperature and it was diluted with dichloromethane. Acetic acid was added to help to dissolve the sticky residue. The reaction was washed with NH₄OAc buffer and the organic layer was dried over sodium sulfate and evaporated. The residue was purified by flash chromatography using 0.5% of acetic acid in a mixture of 30% of THF in toluene. The resulting product was co-evaporated twice with ethanol and foamed by co-evaporation twice with acetone to yield the free acid.

p.m.r. ((CD$_3$)$_2$CO) δ: 2.2 (m, 2H), 2.6 (t, 4H), 2.7–3.0 (m, 8H), 5.3 (s, 1H), 7.1–7.35 (m, 3H), 7.4 (s, 1H), 7.5 (d, 1H), 7.55 (dd, 1H), 7.9 (d, 1H), 8.1 (d, 1H), 8.3 p.p.m. (d, 1H).

Dissolution of the acid in ethanol, addition of aqueous sodium hydroxide (0.45 mL of 2N) and co-evaporation twice with ethanol afforded with title compound as a light-yellow solid.

EXAMPLE 20

SODIUM 5-(3-(7-CHLOROQUINOLIN-2-YLMETHYLTHIO)-PHENYL)-8-DIMETHYLCARBAMYL-4,6-DITHIAOCTANOATE

Step 1

Preparation of 3-(methylthio)phenylbromide

To a solution of 3-bromothiophenol (10 g) in acetone (250 mL) was added potassium carbonate (14.6 g) and iodomethane (4.28 mL). The heterogenous mixture was refluxed for 4 hrs., cooled to room temperature, filtered, and concentrated under reduced pressure. Ether (200 mL) was added, and the mixture was filtered again and finally evaporated to dryness to yield the title compound.
$^1$H NMR (CDCl$_3$) δ: 2.46 (s, 3H), 7.10–7.55 (m, 4H).

Step 2

Preparation of 3-(methylthio)benzaldehyde

Magnesium (1.34 g) was flushed with nitrogen for 30 minutes, then heated with a flame. After cooling down to room temperature, THF (35 mL) was added. A small amount of 3-(methylthio)phenylbromide from Step 1 (11.17 g/25 mL THF) was added then a crystal of I$_2$. After the reaction had started, the rest of the bromo compound was added. The mixture was stirred at room temperature for 4 hrs. Then triethyl orthoformate (30 mL/10 mL THF) was added and the solution was refluxed for 78 hrs. After cooling to room temperature, 1N HCl was added, the mixture was stirred for 1 hr, then extracted with ether, washed with brine, dried over Na$_2$SO$_4$, filtered and evaporated to dryness. Purification by chromatography afforded 3-(methylthio)benzaldehyde.

Step 3

Preparation of 3-(7-chloroquinolin-2-ylmethylthio)benzaldehyde

To 3-(methylthio)benzaldehyde (1.8 g) in CHCl$_3$ at 0° C. was slowly added 3-chloroperoxybenzoic acid (2.48 g). The mixture was stirred for 1 hr at 0° C. then warmed-up to room temperature. Calcium hydroxide (1.3 g) was added and the suspension was stirred for 20 min at room temperature then filtered over celite and evaporated to dryness. To the oily residue trifluroacetic anhydride (20 mL) was added, and evaporated under reduced pressure. This process was repeated. To the oily residue 75 mL of 0.4N sodium hydroxide and 75 mL of methanol were added with vigorous stirring. The solution was extracted with ether, dried Na$_2$SO$_4$, filtered and evaporated to dryness. The residue was dissolved in 20 mL of acetone, potassium carbonate (1.26 g) and 2-bromomethyl-7-chloroquinoline from Example 4, Step 1 (1.5 g) were added. The mixture was refluxed for 15 min, then cooled to room temperature, ether was added, the organic layer was washed with brine (3×), dried over sodium sulfate, filtered and evaporated to dryness. Purification by chromatography afforded the title compound.
$^1$H NMR (CDCl$_3$) δ: 4.48 (s, 2H), 7.38–8.11 (m, 9H), 9.93 (s, 1H).

Step 4

Preparation of 5-(3-(7-chloroquinolin-2-ylmethylthio)phenyl)-4,6-dithianonanedioic acid To a solution of aldehyde (Step 3) (500 mg) in toluene (15 mL) was added 3-mercaptopropionic acid (0.56 mL) and p-toluene sulfonic acid (153 mg). The solution was refluxed for 6 hrs in a flask equipped with a Dean-Stark apparatus filled with 3 Ⓒ molecular sieve. The solution was cooled to room temperature, methylene chloride was added, the organic layer was washed with acidified 25% ammonium acetate, dried over sodium sulfate filtered and evaporated to dryness to afford the title compound.
$^1$H NMR (CDCl$_3$) δ: 2.62–2.98 (m, 8H), 4.46 (s, 2H), 5.00 (s, 1H), 7.08–8.08 (m, 9H).

Step 5

To a solution of diacid (Step 4) (360 mg) in dichloromethane (28 mL) and acetonitrile (7.1 mL) was added 2-chloro-1-methylpyridinium iodide (227 mg). The solution was cooled to 0 C. and triethylamine (123 μL) was added. After stirring for 15 min, 0.42 mL of a 2M solution of dimethylamine in toluene was added. The solution was stirred 1 hr at room temperature, washed with acidified 25% ammonium acetate, dried over sodium sulfate, filtered and evaporated to dryness. To the oil obtained after chromatography, in 2 mL of ethanol, was added 0.154 mL of 2N NaOH. After evaporating to dryness the title compound was obtained as a foam.
$^1$H NMR δ: 2.52–2.96 (m, 8H), 2.92 (s, 6H), 4.42 (s, 2H), 4.96 (s, 1H), 7.10–8.12 (m, 9H).

EXAMPLE 21

8-CARBAMYL-5-(3-(7-CHLOROQUINOLIN-2-YLMETHYLTHIO)PHENYL-4,6-DITHIAOCTANOIC ACID

To 500 mg of diacid (Example 20, Step 4) in dichloromethane (39 mL) and acetonitrile (9.9 mL) at 0° C. was added 2-chloro-1-methylpyridinium iodide (315 mg). After 15 min triethylamine (170 μL) and 10 mL of a saturated solution of ammonia in ether were added. The solution was stirred 1 hr at room temperature then it was washed with acidified 25% ammonium acetate, extracted with ethyl acetate, dried over sodium sulfate, filtered and evaporated to dryness. Purification by chromatography afforded the title compound.
m.p. 141°–142° C., $^1$H NMR (CDCl$_3$) δ: 2.44 (t, J=7 Hz, 4H), 2.68 (m, 2H), 2.92 (m, 2H), 4.41 (s, 2H), 4.94 (s, 1H), 5.58(s, 1H), 6.16 (s, 1H), 7.14–8.12 (m, 9H).

EXAMPLE 22

N-t-BUTYL-8-(1H-TETRAZOL-5-YL)-5-(3-(7-CHLOROQUINOLIN-2-YLMETHOXY)PHENYL)-4,6-DITHIAOCTAMIDE

Step 1

Preparation of 5-(3-(7-chloroquinolin-2-ylmethoxy)phenyl)-8-cyano-4,6-dithiaoctanoic acid To the amide acid (Example 17) (2.788 g, 3.63 mmoles) in THF (40 mL) at −23° C., pyridine (2.2 mL, 7.5 equiv.) and trifluoroacetic anhydride (1.1 mL, 2.2 equiv.) were added. After one hour of stirring at 0° C., 10% HCl was added, the mixture was extracted with EtOAc, dried over sodium sulfate and evaporated.

Flash chromatography on silica with EtOAc:-toluene:AcOH 30:70:1 afforded 1.447 g of the title compound.

IR (neat) ν 3600–2500 (COOH), 2245, 1705, 1600, 1495 cm$^{-1}$; $^1$H NMR (CD$_3$COCD$_3$) δ: 2.61 (t, 2H), 2.68–2.97 (m, 6H), 5.32 (s, 1H), 5.38 (s, 2H), 7.02 (dd, 1H), 7.08–7.33 (m, 3H), 7.54 (dd, 1H), 7.70 (d, 1H), 7.94 (d, 1H), 8.03 (broad s, 1H), 8.35 p.p.m. (d, 1H).

Step 2

Preparation of
N-t-butyl-5-(3-(7-chloroquinolin-2-yl-methoxy)phenyl)-8-cyano-4,6-dithiaoctanamide Dimethylformamide (50 μL) was added to a solution of the crude cyanoacid (step 1) (1.477 g) in CH$_2$Cl$_2$ (25 mL), followed, at 0° C., by oxalyl chloride (400 μL). The solution was stirred at room temperature for 15 minutes. At 0° C., t-butylamine (3.3 mL) was then added and the mixture stirred at room temperature 2 hours. Addition of 25% aqueous NH$_4$OAc, extraction with EtOAc, drying, evaporation, and flash chromatography on silica with ethyl acetate:toluene 25:75 and 30:70 afforded the title compound.

$^1$H NMR (CD$_3$COCD$_3$) δ: 1.30 (s, 9H), 2.36 (t, 2H), 2.65–2.95 (m, 6H), 5.29 (s, 1H), 5.39 (s, 2H), 6.74 (broad s, 1H), 7.02 (dd, 1H), 7.09–7.35 (m, 3H), 7.59 (dd, 1H), 7.73 (d, 1H), 8.01 (d, 1H), 8.04 (broad s, 1H), 8.40 (d, 1H) p.p.m.

Step 3

The cyanoamide (step 2) (503 mg) was mixed with tributyltin azide (566 mg, 1.5 equiv.) and heated at 120° C. for 4 hours. Flash chromatography of the crude reaction mixture on silica using THF:toluene:AcOH 30:70:1 afforded the title compound.

$^1$H NMR (CD$_3$COCD$_3$) δ: 1.35 (s, 9H), 2.45–2.53 (m, 2H), 2.64–2.76 (m, 1H), 2.86–3.05 (m, 3H), 3.29 (t, 2H), 5.17 (s, 1H), 5.38 (s, 2H), 6.98–7.09 (m, 2H), 7.18–7.21 (m, 2H), 7.30 (dd, 1H), 7.61 (dd, 1H), 7.76 (d, 1H), 8.01 (d, 1H), 8.05 (broad s, 1H), 8.42 (d, 1H) p.p.m.

EXAMPLE 23

8-CARBAMYL-5-(3-(7-CHLOROQUINOLIN-2-YLMETHOXY)PHENYL)-4,6-DITHIAOCTANAMIDE

Using the procedure described in Example 16 by replacing 1 eq 2-chloro-1-methyl pyridinium iodide by 2 eq of 2-chloro-1-methylpyridinium iodide and t-butylamine by excess ammonia gas in Step 3 there was obtained the title compound.

p.m.r. (CD$_3$SOCD$_3$) δ: 8.3 (d, 1H), 8.0 (d, 1H), 7.9 (d, 1H), 7.7 (d, 1H), 7.5 (dd, 1H), 7.0–7.3 (m, 3H), 7.0 (d, 1H), 6.9 (bd, 1H), 6.7 (bs, 1H), 5.3 (s, 2H), 5.05 (s, 1H), 2.6–2.85 (m, 4H), 2.36 p.p.m. (t, 4H).

EXAMPLE 24

5-(3-(2-(7-CHLOROQUINOLIN-2-YL)CYCLOPROPYL)PHENYL-4,6-DITHIANONANEDIOIC ACID

Step 1

Preparation of
3-(2-(7-chloroquinolin-2-yl)ethenyl)benzaldehyde

A solution of isophthalaldehyde (4.0 g) and 7-chloroquinaldine (5.39 g) in acetic anhydride was heated at 125° C. in an oil bath for 48 hours. The reaction was cooled to room temperature, diluted with ether (30 mL) and the resulting suspension was stirred vigorously. The solid title compound was collected by filtration and was used as such in the next step.

Step 2

Preparation of
2-(3-(2-(7-chloroquinolin-2-yl)ethenyl)phenyl)-1,3-dioxolane

A mixture of 3-(2-(7-chloroquinolin-2-yl)ethenyl)benzaldehyde (step 1) (938 mg, 3.19 mmoles), ethylene glycol (200 μL, 1.15 equiv.), p-toluene-sulfonic acid (296 mg, 0.5 equiv.) and toluene (1.5 mL) was heated at reflux overnight. 25% aqueous NH$_4$OAc was then added and the mixture extracted with EtOAc. Flash chromatography of the residue on silica with EtOAc:-hexane 20:80 afforded the title compound.

$^1$H NMR (CD$_3$COCD$_3$) δ: 4.00–4.20 (m, 4H), 5.80 (s, 1H), 7.42–7.56 (m, 4H), 7.74 (m, 1H), 7.80–8.03 (m, 5H), 8.33 (d, 1H), p.p.m.

Step 3

Preparation of
2-(3-(2-(7-chloroquinolin-2-yl)cyclopropyl)phenyl)1,3-dioxolane

To a solution of trimethylsulfonium iodide (2.128 g, 10.4 mmoles) in 20 mL of anhydrous THF at −10° C. was added dropwise a solution of n-butyllithium 1.6M in hexanes (4.9 mL, 0.75 equiv.). Then the temperature was raised to 21° C. for 2 hours. To this mixture cooled to 0° C., the alkene (step 2) (967 mg, 2.86 mmoles) in 5 mL THF was added and the solution stirred overnight. Hydrolysis with 25% aqueous NH$_4$OAc, extraction with EtOAc and flash chromatography on silica using EtOAc:toluene 2.5:97.5 afforded the title compound.

$^1$H (CD$_3$COCD$_3$) δ: 1.61 (m, 1H), 1.94 (m, 1H), 2.56 (m, 1H), 2.70 (m, 1H), 3.93–4.14 (m, 4H), 5.71 (s, 1H), 7.21–7.36 (m, 4H), 7.48 (dd, 1H), 7.55 (d, 1H), 7.90 (d, 1H), 7.92 (s, 1H), 8.21 (d, 1H) p.p.m.

Step 3

Preparation of
3-(2-(7-chloroquinolin-2-yl)cyclopropyl)benzaldehyde

The dioxolane (step 3) (500 mg, 1.42 mmoles) was heated at reflux in 9 mL of THF:AcOH:H$_2$O 6:2:1 for 2 hours. Addition of 25% NH$_4$OAc, extraction with EtOAc, drying, evaporation, and flash chromatography on silica with EtOAc:toluene 2.5:97.5 afforded the title compound.

$^1$H NMR (CD$_3$COCD$_3$) δ: 1.67 (m, 1H), 2.00 (m, 1H), 2.67 (m, 1H), 2.81 (m, 1H), 7.46–7.63 (m, 4H), 7.72–7.81 (m, 2H), 7.90–7.95 (m, 2H), 8.24 (d, 1H), 10.04 (s, 1H), p.p.m.

Step 4

A solution of aldehyde (step 4) (387 mg, 1.26 mmoles), 3-mercaptopropionic acid (440 μL, 4 equiv.) and p-toluenesulfonic acid (126 mg, 0.5 equiv.) in toluene (6 mL) was heated at reflux for 4:30 hours using a Dean-Stark trap to remove water. To the cooled reaction mixture 50 mL of 25% NH$_4$OAc and 4 mL of AcOH were added. Extraction with CH$_2$Cl$_2$, drying, evaporation, and flash chromatography on silica with acetone:CH$_2$Cl$_2$:AcOH 15:85:1 afforded the title compound.

¹H NMR (CD₃COCD₃) δ: 1.62 (m, 1H), 1.94 (m, 1H), 2.59 (t, 4H), 2.64–2.94 (m, 6H), 5.25 (s, 1H), 7.12–7.41 (m, 4H), 7.48 (d, 1H), 7.56 (d, 1H), 7.89–7.95 (m, 2H), 8.23 (d, 1H) p.p.m.; MS 501 (M+), 395 (M-C₃H₆SO₂), 322 (M-C₃H₆SO₂-C₃H₅O₂), 177.

EXAMPLE 25

5-(3-(2-(7-CHLOROQUINOLIN-2-YL)ETHYL)-PHENYL)-4,6-DITHIANONANEDIOIC ACID

Step 1

Preparation of
3-(2-(7-chloroquinolin-2-yl)ethyl)benzonitrile

To a solution of 7-chloroquinaldine (17.7 g) in THF (80 mL) at −78° was added a solution of 100 mL lithium diisopropyl amide (LDA) (1M) dropwise. After addition the solution was warmed to −20° and added dropwise to 3-cyanobenzyl bromide (20 g) in THF (80 mL) at 0°. The reaction mixture was stirred 1 hr at 0° and warmed to room temperature (30 min). The mixture was partitioned between pH 7 buffer (25% NH₄OAc) and ethyl acetate. The organic layer was dried and evaporated. Flash chromatography of the residue using 30% ether in hexane afforded the title compound.
p.m.r. (CDCl₃) δ: 8.1 (d, 1H), 7.9 (d, 1H), 7.0–7.8 (m, 7H), 3.2 p.p.m. (m, 4H).

Step 2

Preparation of
3-(2-(7-chloroquinolin-2-yl)ethyl)benzaldehyde

To the cyanide (Step 1, 10 g) in formic acid (200 mL) at 100° was added portionwise Ni-Al alloy (3 g). The reaction mixture was heated at 110° for 6 hrs, filtered and evaporated. The residue was partitioned between NaHCO₃ (aq) and ethyl acetate, and the organic layer was dried and evaporated. Flash chromatography using 30% ether in hexane afforded the title compound.
p.m.r. (CDCl₃) δ: 9.9 (s, 1H), 8.1 (d, 1H), 7.9 (d, 1H), 7.0–7.8 (m, 7H), 3.2 p.p.m. (m, 4H).

Step 3

A solution of aldehyde (Step 2, 2 g), 3-mercaptopropionic acid (4 mL) and TsOH (0.5 g) in toluene (25 mL) was heated 8 hrs at reflux using a Dean Stark trap. The mixture was partitioned between pH 7 buffer (100 mL), acetic acid (5 mL) and CH₂Cl₂ (500 mL). The organic layer was dried (Na₂SO₄) and evaporated. Flash chromatography of the residue using 15% THF in toluene with 0.5% AcOH afforded the title compound.
m.p. 160°–161° p.m.r. (CD₃COCD₃) δ: 8.25 (d, 1H), 8.0 (d, 1H), 7.95 (d, 1H), 7.55 (dd, 1H), 7.45 (d, 1H), 7.4 (bs, 1H), 7.15–7.35 (m, 3H), 5.20 (s, 1H), 2.95–2.75 (m, 4H), 2.65–2.85 (m, 4H), 2.50 p.p.m. (t, 4H).

EXAMPLE 26

5-(3-(2-(7-CHLOROQUINOLIN-2-YL)ETHYL)-PHENYL)-8-DIMETHYLCARBAMYL-4,6-DITHIAOCTANOIC ACID

To a suspension of diacid (Example 25) (0.3 g) in dichloromethane (20 mL), acetonitrile (5 mL) and triethylamine (200 μL) was added 2-chloro-1-methylpyridinium iodide (180 mg). The mixture was stirred 30 min, cooled to 0° and 0.32 mL of a 2M solution of dimethylamine in toluene was added. The reaction was stirred 2 hours at room temperature. The reaction mixture was poured onto NH₄OAc buffer and acetic acid (5 mL) was added. The mixture was extracted with ethyl acetate, which was dried over sodium sulfate and evaporated. Purification of the residue by flash chromatography starting with 15% and finishing with 30% of THF in toluene containing 1% of acetic acid afforded the title compound.
p.m.r. (CD₃COCD₃, CD₃SOCD₃) δ: 8.28 (d, 1H), 8.0 (d, 1H), 7.95 (d, 1H), 7.55 (dd, 1H), 7.45 (d, 1H), 7.38 (bs, 1H), 7.15–7.32 (m, 3H), 5.23 (s, 1H), 3.1–3.3 (m, 4H), 2.95 (s, 3H), 2.85 (s, 3H), 2.4–2.8 p.p.m. (m, 8).

EXAMPLE 27

(+)-5-(3-(2-(7-CHLOROQUINOLIN-2-YL)E-THENYL)PHENYL)-8-DIMETHYLCARBAMYL-4,6-DITHIAOCTANOIC ACID

Step 1

Preparation of 3-hydroxymethylbenzaldehyde

To a solution of isophtalaldehyde (8 g) in ethanol (80 mL) at room temperature was added NaBH₄ portion wise, until about 50% reaction by TLC. The reaction mixture was quenched with 25% ammonium acetate, extracted with ethyl acetate, which was washed with brine (2×), dried over sodium sulfate, filtered and evaporated to dryness. Purification of the residue by flash chromatography using 50% ether in hexane afforded the pure title compound.
¹H NMR (CDCl₃) δ 2.45 (s, 1H, OH), 4.78 (s, 2H, C$\underline{H_2}$OH), 7.50–7.90 (m, 4H, Ar), 10.05 (s, 1H, CHO).

Step 2

Preparation of
3-t-butyldiphenylsilyloxymethylbenzaldehyde

To a solution of 3-hydroxymethylbenzaldehyde (step 1) (3 g) in methylene chloride (15 mL) and triethylamine (4.1 mL) was slowly added t-butylchlorodiphenyl silane (8 mL). Finally, a few mgs of 4-pyrrolidinopyridine was added as a catalyst. The reaction mixture was stirred overnight at room temperature (R.T.). The solution was quenched with 25% ammonium acetate and extracted with ethyl acetate, which was washed with brine (2×), dried over sodium sulfate, filtered and evaporated to dryness. Purification by flash chromatography, using 4% ethyl acetate in hexane afforded the title compound.
¹H NMR (CDCl₃) δ 1.13 (s, 9H, t-Bu), 4.82 (s, 2H, CH₂O), 7.25–7.85 (m, 14H, Ar), 10.05 (s, 1H, CHO).

Step 3

Preparation of (R)-(+)-α-methoxybenzenethanethioic acid

To (R)-(−)-α-methoxyphenylacetic acid (2 g) in benzene (20 mL) at −10° C. was slowly added oxalyl chloride (1.15 mL) and 1 drop of DMF. The solution was slowly warmed up to room temperature and stirred for 2 hrs. The solvent was evaporated and the oily residue was coevaporated with toluene (3×). This acid chloride was used as such. I.R. (neat) 1790 cm⁻¹ (C=O).

To ethanol (20 mL) at −10° C., anhydrous NaSH (1.34 g, 2 eq) was added. Then, the acid chloride in THF (8 mL) was slowly added. The reaction mixture was stirred for 20 min at −10° C. The mixture was acidified with 6N HCl, extracted with EtOAc, washed with brine (2×), dried Na₂SO₄, filtered and evaporated to dryness to afford (R)-(+)-α-methoxybenzenethanethioic acid.
[α]$_D^{25}$ +32.7 (C=3.1, acetone). IR (neat) 2550 (SH) and 1700 cm⁻¹ (C=O).

Step 4

Preparation of 3-mercapto-N,N-dimethylpropanamide

To N,N-dimethylacrylamide (19.8 g, 0.2 mol) at 0° C., was slowly added thioacetic acid (15.22 g, 0.2 mol). The ice-bath was then removed and the reaction mixture stirred at room temperature for 15 min. On distillation (b.p. 96°-98°/0.06 Tor) a reddish oil was obtained.

To this oil (5.66 g, 32.34 mmol.) in methanol (20 mL) at 0° C. was added potassium t-butoxide (3.622 g, 1 eq) in 3 portions. The mixture was stirred at room temperature for 1.5 hr. The reaction mixture was poured over 25% ammonium acetate and methylene chloride. 2N HCl was added to bring the pH to 7.0-7.5. After 2 more extractions with methylene chloride, the organic layers were combined, dried over sodium sulfate, filtered, and evaporated to dryness to afford 3-mercapto-N,N-dimethylpropanamide as a pale orange oil.

Step 5

Preparation of (−)-methyl 5-(3-(t-butyldiphenylsilyloxymethyl)phenyl)-8-dimethylcarbamyl-4,6-dithiaoctanoate To a solution of 3-t-butyldiphenylsilyloxymethylbenzladehyde (step 2) (8.98 g, 24 mmol.) in benzene (90 mL) was added 3-mercapto-N,N-dimethylpropanamide (step 4) (3.5 g, 26 mmol.), (R)-(+)-α-methoxybenzenethanethioic acid (step 3) (4.76 g, 26 mmol.) and p-toluenesulfonic acid (2.26 g, 13 mmol.). The solution was refluxed for 3.5 hrs with a Dean-Stark apparatus filled with activated 3A molecular sieve. The solution was cooled to room temperature, quenched with 25% ammonium acetate, and extracted with EtOAc, which was washed with brine (3×), dried over sodium sulfate, filtered and evaporated to dryness. The two diastereomers were separated by flash chromatography using 40% of ethyl acetate in hexane. Less polar compound:
$^1$H NMR (CDCl$_3$) δ 1.12 (s, 9H, t-Bu), 2.45 (t, 2H, J=7 Hz, CH$_2$), 2.78 (t, 2H, J=7 Hz, CH$_2$), 2.82 and 2.88 (2s, 6H, N(CH$_3$)$_2$), 3.42 (s, 3H, OCH$_3$), 4.70 (s, 1H, CH), 4.74 (s, 2H, CH$_2$O), 5.61 (s, 1H, CH), 7.26-7.71 (m, 19H, Ar). More polar compound:
$^1$H NMR (CDCl$_3$) δ 1.10 (s, 9H, t-Bu), 3.59 (t, 2H, J=7 Hz, CH$_2$), 3.85 (t, 2H, J=7 Hz, CH$_2$), 3.95 and 3.96 (2s, 6H, N(CH$_3$)$_2$), 3.48 (s, 3H, OCH$_3$), 4.72 (s, 2H, CH$_2$O), 4.78 (s, 1H, CH), 5.64 (s, 1H, CH), 7.26-7.85 (m, 19H, Ar).

A solution of the less polar compound (2.6 g, 3.87 mmol.) in THF (40 mL) was cooled to −78° C. A solution of sodium methoxide (1M) in methanol (3.47 mL, 0.9 eq) was added. After stirring for 10 min (−78° C.), methyl acrylate (0.52 mL, 1.5 eq) was added and the solution was stirred for 2 hrs at −78° C. The reaction mixture was quenched at low temperature with a saturated solution of ammonium chloride, and extracted with EtOAc, which was washed with brine (3×), dried over sodium sulfate, filtered and evaporated to dryness. Purification by flash chromatography using 40% ethyl acetate in hexane afforded the title compound.
[α]$_D^{25}$ −1.62 (C=1.22, acetone).
$^1$H NMR (CDCl$_3$) δ 1.12 (s, 9H, t-Bu), 2.50-2.90 (m, 8H, 4(CH$_2$)), 2.91 and 2.92 (2d, 6H, N(CH$_3$)$_2$), 3.68 (s, 1H, OCH$_3$), 4.77 (s, 2H, CH$_2$O), 5.00 (s, 1H, CH), 7.27-7.72 (m, 14H, Ar).

Step 6

Preparation of (−)-methyl 5-(3-(hydroxymethyl)phenyl)-8-dimethylcarbamyl-4,6-dithiaoctanoate To a solution of (−)-methyl 5-(3-(t-butyldiphenylsilyloxymethyl)phenyl)-8-dimethylcarbamyl-4,6-dithiaoctanoate (step 5) (1.377 g, 2.26 mmol.) in THF (25 mL) at room temperature was slowly added tetra-n-butylammonium fluoride (1M) in THF (2.34 mL). The solution was stirred 2 hrs at room temperature Ethyl acetate was added to the reaction mixture, and the organic layer it was washed with brine (3×), dried over sodium sulfate, filtered and evaporated to dryness. Purification by flash chromatography using 40% acetone in hexane afforded the title compound.
[α]$_D^{25}$ −4.2 (C=2.04, acetone). $^1$H NMR (CDCl$_3$) δ 2.50-2.91 (m, 8H, 4(CH$_2$)), 2.94 and 2.96 (2s, 6H, N(CH$_3$)$_2$), 3.70 (s, 3H, OCH$_3$), 4.69 (s, 2H, CH$_2$OH), 5.05 (s, 1H, CH), 7.26-7.49 (m, 4H, Ar).

Step 7

Preparation of (−)-methyl 5-(3-formylphenyl)-8-dimethylcarbamyl-4,6-dithiaoctanoate To a solution of (−)-methyl 5-(3-(hydroxymethyl)phenyl)-8-dimethylcarbamyl-4,6-dithiaoctanoate (step 6) (679 mg) in ethyl acetate (30 mL) was added activated manganese oxide (1.3 g). The suspension was stirred overnight at room temperature. The suspension was filtered on a pad of silica gel and washed with EtOAc. The solvent was evaporated, affording the title compound.
[α]$_D^{25}$ −6.9 (C=1.73, acetone). $^1$H NMR (CDCl$_3$) δ 2.56-2.94 (m, 8H, 4(CH$_2$)), 2.95 and 2.97 (2s, 6H, N(CH$_3$)$_2$), 3.70 (s, 3H, OCH$_3$), 5.14 (s, 1H, CH), 7.52, 7.80 and 7.98 (t, t and s, 4H, Ar), 10.03 (s, 1H, CHO).

Step 8

Preparation of (−)-methyl 5-(3-(2-(7-chloroquinolin-2-yl)ethenyl)phenyl)-8-dimethylcarbamyl-4,6-dithiaoctanoate To a suspension of 7-chloroquinolin-2-yl-methyltriphenylphosphonium bromide (809 mg, 1.56 mmol.) (Example 4, Step 2) in THF (15 mL) at −78° C., was added a solution of n-BuLi (1.6M) in hexane (0.89 mL, 1.43 mmol.). The mixture was stirred for 0.5 hrs at −78° C. Then, (−)-methyl 5-(3-formylphenyl)-8-dimethylcarbamyl-4,6-dithiaoctanoate (step 7) (480 mg, 1.3 mmol.) in THF (4 mL) was slowly added. The mixture was stirred for 0.5 hr at −78° C. and then warmed up to room temperature and stirred for an additional 2 hrs. A solution of 25% ammonium acetate was added, the mixture was extracted with ethyl acetate, and the extracts were washed with brine (3×), dried over sodium sulfate, filtered and evaporated to dryness. Purification by flash chromatography afforded the title compound.
[α]$_D^{25}$ −4.2 (C=1.28, acetone). $^1$H NMR 2.54-2.93 (m, 8H, 4(CH$_2$)), 2.94 (s, 6H, N(CH$_3$)$_2$), 3.70 (s, 1H, OCH$_3$), 5.08 (s, 1H, CH), 7.34-8.14 (m, 11H, Ar).

Step 9

To a solution of (−)-methyl 5-(3-(2-(7-chloro-quinolin-2-yl)ethenyl)phenyl)-8-dimethylcarbamyl-4,6-dithiaoctanoate (step 8) (640 mg, 1.21 mmol.) in peroxide-free 1,2-dimethoxyethane (15 mL) and water (1.5 mL) was added LiOH (1M, 1.8 mL, 1.8 mmol.). The solution was stirred for 3 hrs at room temperature Water was added and the mixture was washed with EtOAc. The aqueous layer was acidified with 1N HCl, extracted with EtOAc, the extracts were washed with brine (2×), dried over Na$_2$SO$_4$, filtered and evaporated to dryness. The oily residue was coevaporated 3 or 4 times with EtOAc and finally was allowed to crystallize in this solvent overnight at 0° C. Filtration afforded the title compound.

$[\alpha]_D^{25}$ +9.1 (C=0.88, 1% NaHCO$_3$).

$^1$H NMR 2.70–3.19 (m, 8H, 4(CH$_2$)), 3.00 and 3.02 (2s, 6H, N(CH$_3$)$_2$), 5.15 (s, 1H, CH), 7.34–8.14 (m, 11H, Ar).

EXAMPLE 28

(−)-5-(3-(2-(7-CHLOROQUINOLIN-2-YL)ETHENYL)PHENYL)-8-DIMETHYLCARBAMYL-4,6-DITHIAOCTANOIC ACID

Step 1

Preparation of (+)-methyl 5-(3-(t-butyldiphenylsilyloxymethyl)phenyl)-8-dimethylcarbamyl-4,6-dithiaoctanoate To a solution of 3-t-butyldiphenylsilyloxymethylbenzaldehyde (Example 27, step 2) (8.98 g, 24 mmol.) in benzene (90 mL) was added 3-mercapto-N,N-dimethylpropanamide (Example 27, step 4) (3.5 g, 26 mmol.), (R)-(+)-α-methoxybenzenethanethioic acid (Example 27, Step 3) (4.76 g, 26 mmol.) and p-toluenesulfonic acid (2.26 g, 13 mmol.) The solution was refluxed for 3.5 hrs with a Dean-Stark apparatus filled with activated 3A molecular sieves. The solution was cooled to room temperature, quenched with 25% ammonium acetate, and extracted with EtOAc, which was washed wth brine (3×), dried over sodium sulfate, filtered and evaporated to dryness. The two diastereomers were separated by flash chromatography using 40% of ethyl acetate in hexane. Less polar compound:

$^1$H NMR (CHCl$_3$) δ 1.12 (s, 9H, t-Bu), 2.45 (t, 2H, J=7 Hz, CH$_2$), 2,78 (t, 2H, J=7 Hz, CH$_2$), 2.82 and 2.88 (2s, 6H, N(CH$_3$)$_2$), 3.42 (s, 3H, OCH$_3$), 4.70 (s, 1H, CH), 4.74 (s, 2H, CH$_2$O), 5.61 (s, 1H, CH), 7.26–7.71 (m, 19H, Ar).

More polar compound:

$^1$H NMR (CDCl$_3$) δ 1.10 (s, 9H, t-Bu), 3.59 (t, 2H, J=7 Hz, CH$_2$), 3.85 (t, 2H, J=7 Hz, CH$_2$), 3.95 and 3.96 (2s, 6H, N(CH$_3$)$_2$), 3.48 (s, 3H, OCH$_3$), 4.72 (s, 2H, CH$_2$O), 4.78 (s, 1H, CH), 5.64 (s, 1H, CH), 7.26–7.85 (m, 19H, Ar).

A solution of the more polar compound (2.6 g, 3.87 mmol.) in THF (40 mL) was cooled to −78° C. A solution of sodium methoxide 1M in methanol (3.47 mL, 0.9 eq) was added. After stirring for 10 min (−78° C.), methyl acrylate (0.52 mL, 1.5 eq) was added and the solution was stirred for 2 hrs at −78° C. The reaction mixture was quenched at low temperature with a saturated solution of ammonium chloride, and extracted with EtOAc, which was washed with brine (3×), dried over sodium sulfate, filtered and evaporated to dryness. Purification by flash chromatography using 40% ethyl acetate in hexane afforded the title compound.

$[\alpha]_D^{25}$+2.05 (C=1.84, acetone). $^1$H NMR (CDCl$_3$) δ 1.12 (s, 9H, t-Bu), 250–2.90 (m, 8H, 4(CH$_2$)), 2.91 and 2.92 (2d, 6H, N(CH$_3$)$_2$), 3.68 (s, 1H, OCH$_3$), 4.77 (s, 2H, CH$_2$O), 5.00 (s, 1H, CH), 7.27–7.72 (m, 14H, Ar).

Step 2

Preparation of (+)-methyl 5-(3-(hydroxymethyl)phenyl)-8-dimethylcarbamyl-4,6-dithiaoctanoate To a solution of (+)-methyl 5-(3-(3-(t-butyldiphenylsilyloxymethyl)phenyl)-8-dimethylcarbamyl-4,6-dithiaoctanoate (step 1) (1.377 g, 2.26 mmol.) in THF (25 mL) at room temperature was slowly added tetra-n-butylammonium fluoride 1M in THF (2.34 mL). The solution was stirred 2 hrs at room temperature Ethyl acetate was added to the reaction mixture, it was washed with brine (3×), dried over sodium sulfate, filtered and evaporated to dryness. Purification by flash chromatography using 40% acetone in hexane afforded the title compound.

$^1$H NMR (CHCl$_3$) δ 2.50–2.91 (m, 8H, 4(CH$_2$)), 2.94 and 2.96 (2s, 6H, N(CH$_3$)$_2$), 3.70 (s, 3H, OCH$_3$), 4.69 (s, 2H, CH$_2$OH), 5.05 (s, 1H, CH), 7.26–7.49 (m, 4H, Ar).

Step 3

Preparation of (+)-methyl 5-(3-formylphenyl)-8-dimethylcarbamyl-4,6-dithiaoctanoate To a solution of (30)-methyl 5-(3-(hydroxymethyl)-phenyl)-8-dimethylcarbamyl-4,6-dithiaoctanoate (step 2) (679 mg) in ethyl acetate (30 mL) was added activated manganese oxide (1.3 g). The suspension was stirred overnight at room temperature. The suspension was filtered on a pad of silica gel and washed with EtOAc. The solvent was evaporated, affording the title compound.

$[\alpha]_D^{25}$+6.7 (C=1.38, acetone).

$^1$H NMR (CDCl$_3$) δ 2.56–2.94 (m, 8H, 4(CH$_2$)), 2.95 and 2.97 (2s, 6H, N(CH$_3$)$_2$), 3.70 (s, 3H, OCH$_3$), 5.14 (s, 1H, CH), 7.52, 7.80 and 7.98 (t, t and s, 4H, Ar), 10.03 (s, 1H, CHO).

Step 4

Preparation of (+)-methyl 5-(3-(2-(7-chloroquinolin-2-yl)ethenyl)phenyl)-8-dimethylcarbamyl-4,6-dithiaoctanoate To a suspension of 7-chloroquinolin-2-yl-methyltriphenylphosphonium bromide (Example 4, Step 2) (809 mg, 1.56 mmol.) in THF (15 mL) at −78° C., was added a soltuion of n-BuLi (1.6M) in hexane (0.89 mL, 1.43 mmol.). The mixture was stirred for 0.5 hrs at −78° C. Then, (+)-methyl 5-(3-formylphenyl)-8-dimethylcarbamyl-4,6-dithiaoctanoate (step 3) (480 mg, 1.3 mmol.) in THF (4 mL) was slowly added. The mixture was stirred for 0.5 hr at −78° C. and then warmed up to room temperature and stirred for an additional 2 hrs. A solution of 25% ammonium acetate was added, the mixture was extracted with ethyl acetate, and the extracts were washed with brine (3×), dried over sodium sulfate, filtered and evaporated to dryness. Purification by flash chromatography afforded the title compound.

$[\alpha]_D^{25}$+3.5 (C=1.74, acetone).

$^1$H NMR 2.54–2.93 (m, 8H, 4(CH$_2$)), 2.94 (s, 6H, N(CH$_3$)$_2$), 3.70 (s, 1H, OCH$_3$), 5.08 (s, 1H, CH), 7.34–8.14 (m, 11H, Ar).

Step 5

To a solution of (+)-methyl 5-(3-(2-(7-chloroquinolin-2-yl)ethenyl)phenyl)-8-dimethylcarbamyl-4,6- dithiaoctanoate (step 4) (640 mg, 1.21 mmol.) in peroxide free 1,2-dimethoxyethane (15 mL) and water (1.5 mL) was added LiOH (1M, 1.8 mL, 1.8 mmol.). The solution was stirred for 3 hrs at room temperature Water was added and the mixture was washed with EtOAc. The aqueous layer was acidified with 1N HCl, extracted with EtOAC, the extracts were washed with brine (2×), dried over $Na_2SO_4$, filtered and evaporated to dryness. The oily residue was coevaporated 3 or 4 times with EtOAc and finally was allowed to crystallize in this solvent overnight at 0° C. Filtration afforded the title compound.

$[\alpha]_D^{25} -9.2$ (C=0.68, 1% $NaHCO_3$).

$^1$H NMR 2.70-3.19 (m, 8H, 4($CH_2$)), 3.00 and 3.02 (2s, 6H, N($CH_3$)$_2$), 5.15 (s, 1H, CH), 7.34-8.14 (m, 11H, Ar).

EXAMPLE 29

5-(3-(2-(7-CHLOROQUINOLIN-2-YL)ETHENYL)-PHENYL)-3,7-DIMETHYL-4,6-DITHIANONANEDIOIC ACID

Using the procedure of Example 1 by substituting methyl 3-mercaptobutanoate for methyl 3-mercaptopropanoate in Step 1 there was obtained the title compound.

p.m.r. (($CD_3$)$_2$CO) δ: 1.3 (m, 6H), 2.3 to 2.8 (m, 4H), 3.2 to 3.4 (m, 2H), 5.45 (t, 1H), 7.4 to 7.6 (m, 4H), 7.7 (bd, 1H), 7.85 to 8.0 (m, 4H), 8.05 (d, 1H), 8.35 p.p.m. (d, 1H).

EXAMPLE 30

5-(3-(7CHLOROQUINOLIN-2-YLMETHOXY)-PHENYL)-3,3,7,7-TETRAMETHYL-4,6-DITHIANONANEDIOIC ACID

Using the procedure of Example 16 (Step 2) by substituting 3-methyl-3-mercaptobutanoic acid for 3-mercaptopropanoic acid in Step 3 there was obtained the title compound.

p.m.r. (($CD_3$)$_2$SO) δ: 1.05 (s, 6H), 1.2 (s, 6H), 2.4 (q, 4H), 5.15 (s, 2H), 5.30 (s, 3H), 6.7 (dd, 1H), 6.9 (d, 1H), 7.0 (m, 1H), 7.35 (dd, 1H), 7.5 (d, 1H), 7.65 (m, 2H), 7.85 (d, 1H), 8.1 p.p.m. (d, 1H).

Using the methods described in the preceding examples, the following compounds are prepared.

EXAMPLE 31

5-(3-(2-(7-TRIFLUOROMETHYLQUINOLIN-2-YL)ETHENYL)PHENYL)-8-N-DIMETHYLCARBAMYL-4,6-DITHIAOCTANOIC ACID

EXAMPLE 32

8-N-t-BUTYLCARBAMYL-5-(3-(6-(METHANESULFONYL)QUINOLIN-2-YLMETHOXY)PHENYL)-4,6-DITHIAOCTANOIC ACID

EXAMPLE 33

5-(3-(7-FLUOROQUINOLIN-2-YL-METHYLTHIO)PHENYL)-4,6-DITHIANONANEDIOIC ACID

EXAMPLE 34

8-CARBAMYL-5-(3-(2-(6-CYANOQUINOLIN-2-YL)ETHENYL)PHENYL)-4,6-DITHIAOCTANAMIDE

EXAMPLE 35

8-(N-METHANESULFONYL)CARBAMYL)-5-(3(2-(7-CHLOROQUINOLIN-2-YL)ETHENYL)-PHENYL)-4,6-DITHIAOCTANOIC ACID

EXAMPLE 36

9-HYDROXY-5-(3-(6,7-DIFLUOROQUINOLIN-2-YLMETHOXY)PHENYL)-4,6-DITHIANONANOIC ACID

EXAMPLE 37

9-HYDROXY-5-(3-(2-(7-TRIFLUOROMETHYLTHIO)QUINOLIN-2-YL)ETHENYL)PHENYL)-4,6-DITHIANONANOIC ACID

EXAMPLE 38

8-FORMYL-5-(3-((7-TRIFLUOROMETHANESULFONYL)QUINOLIN-2-YLMETHYLTHIO)-PHENYL)-4,6-DITHIAOCTANOIC ACID

EXAMPLE 39

4-(3-(7-CHLOROQUINOLIN-2-YLMETHOXY)-PHENYL)-3,5-DITHIAHEPTANEDIOIC ACID m.p. 157°-158°
Anal. Calc. $C_{21}H_{18}ClNO_5S_2$
requires: C 54.36, H 3.91, Cl 7.64, N 3.02, S 13.82;
found: C54.70, H 3.96, Cl 7.68, N 3.01, S 14.03.

EXAMPLE 40

SODIUM 6-DIMETHYLCARBAMYL-4-(3-(7-CHLOROQUINOLIN-2-YLMETHOXY)PHENYL)-3,5-DITHIAHEXANOATE MONOHYDRATE

Anal. Calc. $C_{23}H_{22}ClN_2NaO_4S_2 \cdot H_2O$
requires: C 52.02, H 4.56, Cl 6.68, N 5.27, S 12.08;
found: C 51.66, H 4.67, Cl 6.87, N 5.07, S 12.05.

EXAMPLE 41

6-CARBAMYL-4-(3(7-CHLOROQUINOLIN-2-YLMETHOXY)PHENYL)-3,5-DITHIAHEXANOIC ACID m.p. 173° C. after sintering at approx. 145° C.
Anal. Calc. $C_{21}H_{19}ClN_2O_4S$
requires: C 54.48, H 4.14, N 6.05;
found: C 54.44, H 4.27, N 5.97.

EXAMPLE 42

5-(3-(7-FLUOROQUINOLIN-2-YLMETHOXY)-PHENYL)-4,6-DITHIANONANEDIOIC ACID m.p. 139°–140° C.
Anal. Calc. $C_{23}H_{22}FNO_5S_2$
requires: C 58.09, H 4.66, N 2.95, S 13.48;
found: C 58.08, H 4.82, N 3.07, S 13.48.

EXAMPLE 43

8-DIMETHYLCARBAMYL-5-(3-(7-FLUOROQUINOLIN-2-YLMETHOXY)PHENYL-4,6-DITHIAOCTANOIC ACID m.p. 152°–153° C.
Anal. Calc. $C_{25}H_{27}FN_2O_4S_2$
requires: C 59.74, H 5.41, N 5.57, S 12.76;
found: C 59.95, H 5.61, N 5.56, S 12.84.

EXAMPLE 44

5-(3-(7-TRIFLUOROMETHYLQUINOLIN-2-YLMETHOXY)PHENYL)-4,6-DITHIANONANEDIOIC ACID m.p. 156°–157° C.
Anal. Calc. $C_{24}H_{22}F_3NO_5S_2$
requires: C 54.85, H 4.22, N 2.66, S 12.20;
found: C 55.05, H 4.29, N 2.70, S 12.40.

EXAMPLE 45

8-DIMETHYLCARBAMYL-5-(3-(7-TRIFLUOROMETHYLQUINOLIN-2-YLMETHOXY)-PHENYL)-4,6-DITHIAOCTANOIC ACID m.p. 130°–131° C.
Anal. Calc. $C_{26}H_{27}F_3N_2O_4S_2$
requires: C 56.51, H 4.92, N 5.07, S 11.60;
found: C 56.50, H 5.08, N 4.94, S 11.73.

EXAMPLE 46

8-DIMETHYLCARBAMYL-5(3-(2-(7-METHYL-QUINOLIN-2-YL)ETHENYL)PHENYL)-4,6-DITHIAOCTANOIC ACID

What is claimed is:
1. A compound of the formula:

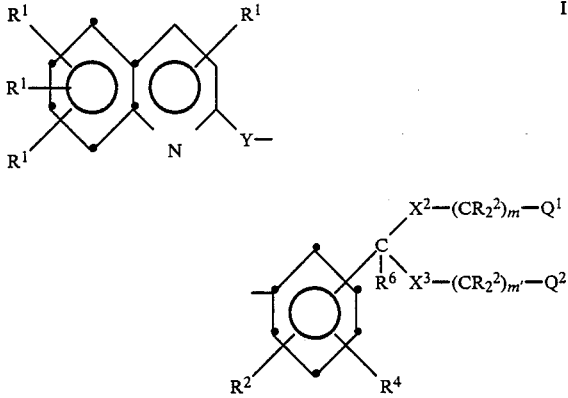

wherein:
$R^1$ is H, halogen, $C_1$–$C_8$ alkyl, $C_2$–$C_8$ alkenyl, $C_2$–$C_8$ alkynyl, —$CF_3$, —$OR^2$, —$SR^2$, —$S(O)R^2$, —$S(O)_2R^2$, —$NR^2R^2$, —CHO, —$COOR^2$, —(C=O)$R^2$, —C(OH)$R^2R^2$, —CH, —$NO_2$, substituted or unsubstituted phenyl, substituted or unsubstituted benzyl, or substituted or unsubstituted phenethyl;

$R^2$ is H, $C_1$–$C_8$ alkyl, $C_2$–$C_8$ alkenyl, $C_2$–$C_8$ alkynyl, —$CF_3$, substituted or unsubstituted phenyl, substituted or unsubstituted benzyl, or substituted or unsubstituted phenethyl;

$R^4$ is H, halogen, —$NO_2$, —CN, —$OR^2$, —$SR^2$, $NR^2R^2$, $C_1$–$C_8$ alkyl, or —(C=O)$R^2$;

$R^6$ is H or $C_1$–$C_4$ alkyl;

$R^{10}$ is H, $C_1$–$C_6$ alkyl, —(C=O)$R^{11}$, unsubstituted phenyl, unsubstituted benzyl, or two $R^{10}$ groups joined to the same N may form a ring of 5 or 6 members containing up to two heteratoms chosen from O, S or N;

$R^{11}$ is H, $C_1$–$C_8$ alkyl, $C_2$–$C_8$ alkenyl, $C_2$–$C_8$ alkynyl, —$CF_3$, or unsubstituted phenyl, benzyl, or phenethyl;

$Q^1$ and $Q^2$ are independently —$COOR^2$ or, —$CONR^{10}R^{10}$;

$X^2$ and $X^3$ are independently O, S, S(O), or $S(O)_2$;

Y is —$CR^2$=$CR^2$—, or —C≡C—; and the pharmaceutically acceptable salts thereof.

2. A compound of claim 1 of the Formula Ia:

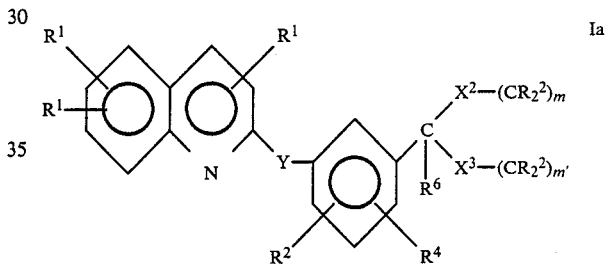

wherein:
Y is —$CR^2$=$CR^2$— or —C≡C—; the other substituents are as defined for Formula I; and the pharmaceutically acceptable salts thereof.

3. A compound of claim 1 of the Formula Ib:

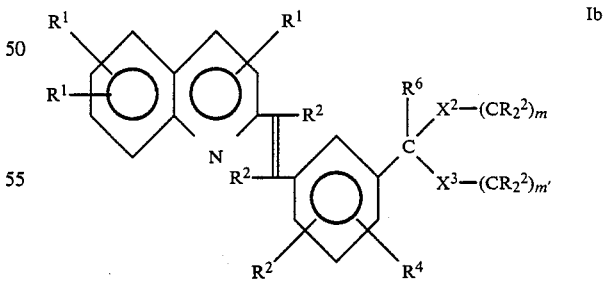

wherein:
$R^1$ is H, halogen, $C_1$–$C_3$ alkyl, —$CF_3$, or $SCF_3$;
$R^2$ is H, $C_1$–$C_3$ alkyl, $C_2$–$C_3$ alkenyl, or —$CF_3$;
$X^2$ and $X^3$ are independently O or S; the other substituents are as defined for Formula I; and the pharmaceutically acceptable salts thereof.

4. A compound of claim 1 of the Formula Ic:

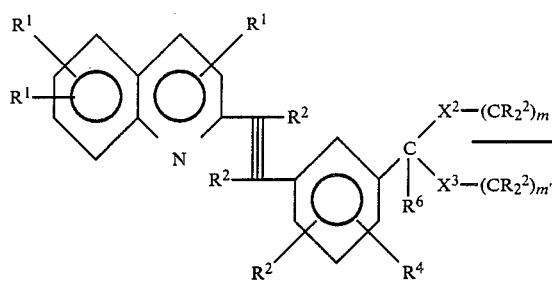

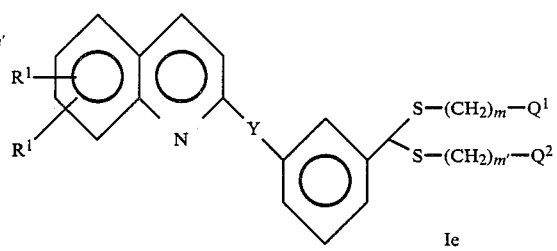

| Compound | R¹,R¹ | m,m' | Y | Q¹ | Q² |
|---|---|---|---|---|---|
| 10 | H,7-Cl | 2,2 | —CH₂O— | —CON(CH₃)₂ | —COOH |
| 11 | H,7-Cl | 2,2 | —CH=CH— | —CON⟨O⟩ | —COOH |
| 12 | H,7-Cl | 1,1 | —CH=CH— | —COOH | —COOH |
| 13 | H,7-Cl | 1,1 | —CH=CH— | —CON(CH₃)₂ | —COOH |
| 14 | H,H | 2,2 | —CH=CH— | —COOH | —COOH |
| 41 | H,7-Cl | 1,1 | —CH₂O— | —COOH | —CONH₂ |
| 42 | H,7-F | 2,2 | —CH₂O— | —COOH | —COOH |
| 43 | H,7-F | 2,2 | —CH₂O— | —COOH | —CON(CH₃)₂ |
| 44 | H,7-CF₃ | 2,2 | —CH₂O— | —COOH | —COOH |
| 45 | H,7-CF₃ | 2,2 | —CH₂O— | —COOH | —CON(CH₃)₂ |
| 46 | H,7-CH₃ | 2,2 | —CH=CH— | —COOH | —CON(CH₃)₂ | wherein:
$R^1$ is H, halogen, $C_1$-$C_3$ alkyl, —$CF_3$, or $SCF_3$;
$R^2$ is H, $C_1$-$C_3$ alkyl, $C_2$-$C_3$ alkenyl, or —$CF_3$;
$X^2$ and $X^3$ are independently O or S; the other substituents are as defined for Formula I; and the pharmaceutically acceptable salts thereof.

5. A compound of claim 1 of Formula Ie which is:

6. A compound of claim 5 which is 4, 6, 13, 27, or 28.
7. A pharmaceutical composition useful in antagonizing leukotriene action in mammals comprising an amount of a compound of claim 1 effective as a leukotriene antagonist and a pharmaceutically acceptable carrier.
8. 5-(3-(2-(7-Chloroquinolin-2-yl)ethenyl)phenyl)-8-dimethylcarbamyl-4,6-dithiaoctanoic acid sodium salt.
9. 5-(3-(2-(7-Chloroquinolin-2-yl)ethenyl)phenyl)-8-dimethylcarbamyl-4,6-dithiaoctanoic acid.

* * * * *

UNITED STATES PATENT AND TRADEMARK OFFICE
CERTIFICATE OF CORRECTION

PATENT NO. : 4,851,409
DATED : July 25, 1989
INVENTOR(S) : Young, et al

It is certified that error appears in the above-identified patent and that said Letters Patent is hereby corrected as shown below:

Amend Claims 1-5 to read as follows:

-- 1. A compound of the formula:

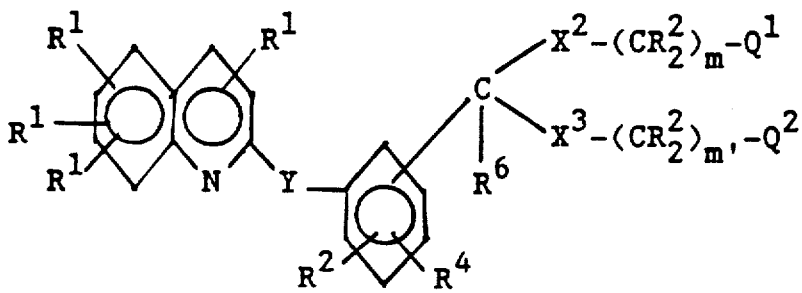

I wherein:

$R^1$ is H, halogen, $C_1$-$C_8$ alkyl, $C_2$-$C_8$ alkenyl, $C_2$-$C_8$ alkynyl, $-CF_3$, $-OR^2$, $-SR^2$, $-S(O)R^2$, $-S(O)_2R^2$, $-NR^2R^2$, $-CHO$, $-COOR^2$, $-(C=O)R^2$, $-C(OH)R^2R^2$, $-CN$, $-NO_2$, substituted or unsubstituted phenyl, substituted or unsubstituted benzyl, or substituted or unsubstituted phenethyl;

$R^2$ is H, $C_1$-$C_8$ alkyl, $C_2$-$C_8$ alkenyl, $C_2$-$C_8$ alkynyl, $-CF_3$, substituted or unsubstituted phenyl, substituted or unsubstituted benzyl, or substituted or unsubstituted phenethyl;

UNITED STATES PATENT AND TRADEMARK OFFICE
CERTIFICATE OF CORRECTION

PATENT NO. : 4,851,409

DATED : July 25, 1989

INVENTOR(S) : Young, et al

It is certified that error appears in the above-identified patent and that said Letters Patent is hereby corrected as shown below:

$R^4$ is H, halogen, $-NO_2$, $-CN$, $-OR^2$, $-SR^2$, $NR^2R^2$, $C_1-C_8$ alkyl, or $-(C=O)R^2$;

$R^6$ is H or $C_1-C_4$ alkyl;

$R^{10}$ is H, $C_1-C_6$ alkyl, $-(C=O)R^{11}$, unsubstituted phenyl, unsubstituted benzyl, or two $R^{10}$ groups joined to the same N may form a ring of 5 or 6 members containing up to two heteratoms chosen from O, S or N;

$R^{11}$ is H, $C_1-C_8$ alkyl, $C_2-C_8$ alkenyl, $C_2-C_8$ alkynyl, $-CF_3$, or unsubstituted phenyl, benzyl, or phenethyl;

m and m' are independently 1-8;

$Q^1$ and $Q^2$ are independently $-COOR^2$ or $-CONR^{10}R^{10}$;

$X^2$ and $X^3$ are independently O, S, S(O), or $S(O)_2$;

Y is $-CR^2=CR^2-$ or $-C\equiv C-$;

and the pharmaceutically acceptable salts thereof.

UNITED STATES PATENT AND TRADEMARK OFFICE
CERTIFICATE OF CORRECTION

PATENT NO. : 4,851,409
DATED : July 25, 1989
INVENTOR(S) : Young, et al

It is certified that error appears in the above-identified patent and that said Letters Patent is hereby corrected as shown below:

2. A compound of Claim 1 of the Formula Ia:

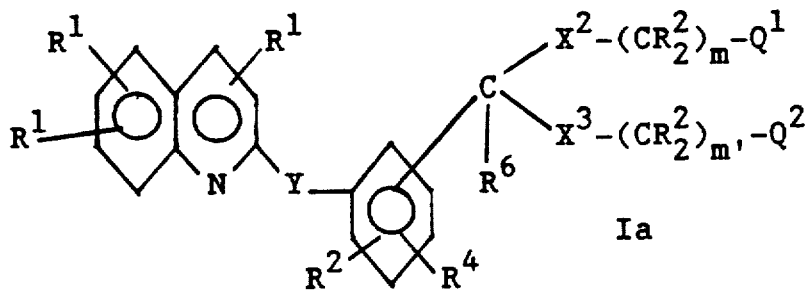

Ia wherein:

Y is $-CR^2=CR^2-$ or $-C\equiv C-$;

the other substituents are as defined for Formula I; and the pharmaceutically acceptable salts thereof.

UNITED STATES PATENT AND TRADEMARK OFFICE
CERTIFICATE OF CORRECTION

PATENT NO. : 4,851,409
DATED : July 25, 1989
INVENTOR(S) : Young, et al

It is certified that error appears in the above-identified patent and that said Letters Patent is hereby corrected as shown below:

3. A compound of Claim 1 of the Formula Ib:

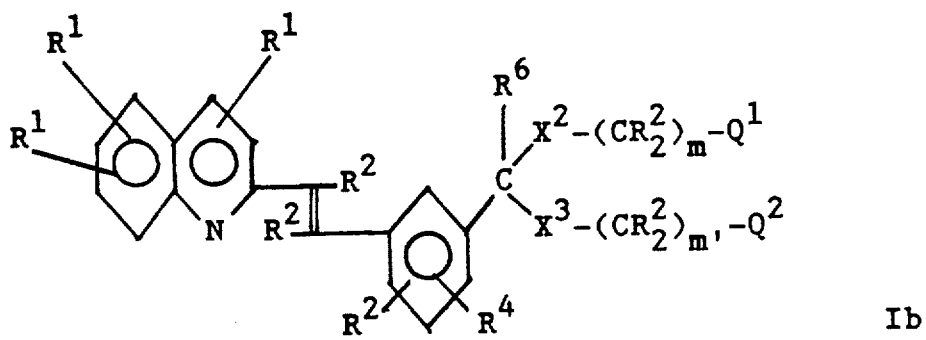

Ib wherein:

$R^1$ is H, halogen, $C_1-C_3$ alkyl, $-CF_3$, or $SCF_3$;

$R^2$ is H, $C_1-C_3$ alkyl, $C_2-C_3$ alkenyl, or $-CF_3$;

$X^2$ and $X^3$ are independently O or S;

the other substituents are as defined for Formula I; and the pharmaceutically acceptable salts thereof.

UNITED STATES PATENT AND TRADEMARK OFFICE
CERTIFICATE OF CORRECTION

PATENT NO. : 4,851,409
DATED : July 25, 1989
INVENTOR(S) : Young, et al It is certified that error appears in the above-identified patent and that said Letters Patent is hereby corrected as shown below:

4. A compound of Claim 1 of the Formula Ic:

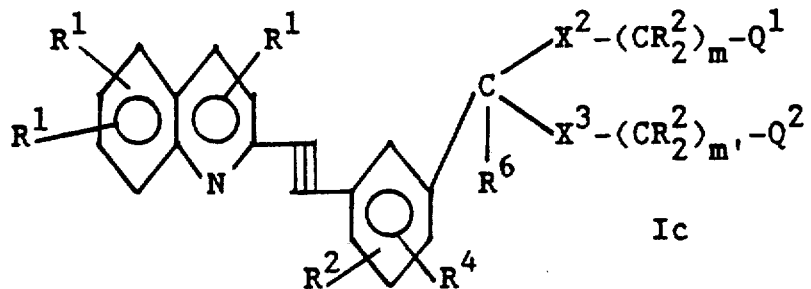

Ic wherein:
$R^1$ is   H, halogen, $C_1$-$C_3$ alkyl, -$CF_3$, or $SCF_3$;
$R^2$ is   H, $C_1$-$C_3$ alkyl, $C_2$-$C_3$ alkenyl, or -$CF_3$;
$X^2$ and $X^3$ are independently O or S;
the other substituents are as defined for Formula I;
and the pharmaceutically acceptable salts thereof.

UNITED STATES PATENT AND TRADEMARK OFFICE
CERTIFICATE OF CORRECTION

PATENT NO. : 4,851,409

DATED : July 25, 1989

INVENTOR(S) : Young, et al

It is certified that error appears in the above-identified patent and that said Letters Patent is hereby corrected as shown below:

5. A compound of Claim 1 of Formula Ie which is:

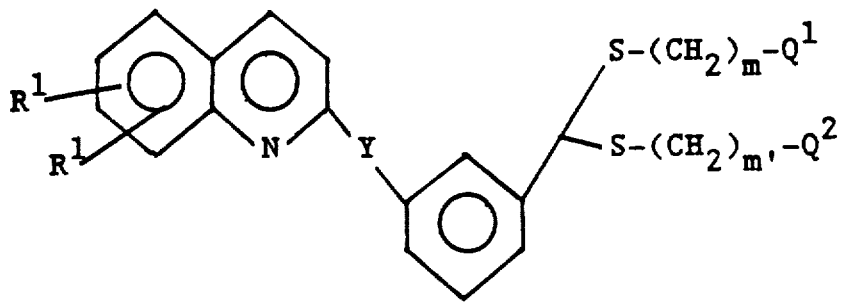

Ie

UNITED STATES PATENT AND TRADEMARK OFFICE
CERTIFICATE OF CORRECTION

PATENT NO. : 4,851,409

DATED : July 25, 1989

INVENTOR(S) : Young, et al

It is certified that error appears in the above-identified patent and that said Letters Patent is hereby corrected as shown below:

| Compound | $R^1, R^1$ | m,m' | Y | $Q^1$ | $Q^2$ |
|---|---|---|---|---|---|
| 1  | H,7-Cl    | 2,2 | -CH=CH- | -COOH         | -COOH |
| 2  | H,7-Br    | 2,2 | -CH=CH- | -COONa        | -COONa |
| 4  | H,7-Cl    | 2,2 | -CH=CH- | -CON(CH$_3$)$_2$ | -COONa |
| 6  | H,7-Cl    | 2,2 | -CH=CH- | -CONH$_2$     | -COOH |
| 8  | H,7-Cl    | 2,2 | -CH=CH- | -CONHCH$_3$   | -COOH |
| 9  | H,7-Cl    | 2,2 | -CH=CH- | -CON(C$_2$H$_5$)$_2$ | -COOH |
| 11 | H,7-Cl    | 2,2 | -CH=CH- |  | -COOH |
| 12 | H,7-Cl    | 1,1 | -CH=CH- | -COOH         | -COOH |
| 13 | H,7-Cl    | 1,1 | -CH=CH- | -CON(CH$_3$)$_2$ | -COOH |
| 14 | H,H       | 2,2 | -CH=CH- | -COOH         | -COOH |
| 15 | 6-Cl,7-Cl | 2,2 | -CH=CH- | -COOH         | -COOH |
| 27 | H,7-Cl    | 2,2 | -CH=CH- | -COOH         | -CON(CH$_3$)$_2$ (+)-isomer |

UNITED STATES PATENT AND TRADEMARK OFFICE
CERTIFICATE OF CORRECTION

PATENT NO. : 4,851,409

DATED : July 25, 1989

INVENTOR(S) : Young, et al

It is certified that error appears in the above-identified patent and that said Letters Patent is hereby corrected as shown below:

| | | | | | |
|---|---|---|---|---|---|
| 28 | H,7-Cl | 2,2 | —CH=CH— | —COOH | —CON(CH$_3$)$_2$ <br> (−)-isomer |
| 31 | H,7-CF3 | 2,2 | —CH=CH— | —COOH | —CON(CH$_3$)$_2$ |
| 34 | H,6-CN | 2,2 | —CH=CH— | —CONH$_2$ | —CONH$_2$ |
| 46 | H,7-CH$_3$ | 2,2 | —CH=CH— | —COOH | —CON(CH$_3$)$_2$ — |

Signed and Sealed this

Twenty-second Day of December, 1992

Attest:

DOUGLAS B. COMER

*Attesting Officer*     *Acting Commissioner of Patents and Trademarks*